[12] United States Patent
Timoszyk et al.

(10) Patent No.: US 12,251,274 B2
(45) Date of Patent: Mar. 18, 2025

(54) SYSTEMS AND METHODS FOR TARGETED SPECTRAL ILLUMINATION

(71) Applicant: Stryker Corporation, Kalamazoo, MI (US)

(72) Inventors: Wojciech Timoszyk, Flower Mound, TX (US); Sean Hastings, Flower Mound, TX (US); Robert York, Lantana, TX (US); Leif Jacobi, Tuttlingen (DE)

(73) Assignee: Stryker Corporation, Portage, MI (US)

( * ) Notice: Subject to any disclaimer, the term of this patent is extended or adjusted under 35 U.S.C. 154(b) by 923 days.

(21) Appl. No.: 16/922,770

(22) Filed: Jul. 7, 2020

(65) Prior Publication Data

US 2021/0007824 A1    Jan. 14, 2021

Related U.S. Application Data

(60) Provisional application No. 62/871,586, filed on Jul. 8, 2019.

(51) Int. Cl.
*A61B 90/35* (2016.01)

(52) U.S. Cl.
CPC .................................. *A61B 90/35* (2016.02)

(58) Field of Classification Search
CPC ... A61B 90/30; A61B 90/35; A61B 2090/306; A61B 2090/309; A61B 1/06; A61B 1/07; A61B 3/0008
See application file for complete search history.

(56) References Cited

U.S. PATENT DOCUMENTS

| 5,611,797 | A  | * | 3/1997 | George | A61B 18/201 |
|  |  |  |  |  | 606/2 |
| 7,520,634 | B2 |  | 4/2009 | Ducharme et al. |  |
| 8,405,324 | B2 |  | 3/2013 | Beers et al. |  |
| 9,057,492 | B2 |  | 6/2015 | Van Herpen et al. |  |
| 2003/0050534 | A1 | * | 3/2003 | Kazakevich | A61B 1/0607 |
|  |  |  |  |  | 600/179 |
| 2004/0095771 | A1 | * | 5/2004 | McDonald | F21V 7/0016 |
|  |  |  |  |  | 362/346 |
| 2005/0099824 | A1 |  | 5/2005 | Dowling et al. |  |

(Continued)

FOREIGN PATENT DOCUMENTS

WO    2004/080291 A2    9/2004

OTHER PUBLICATIONS

Lee et al., (Sep. 1, 2009). "Optimal illumination for discriminating objects with different spectra," Optics Letters 34(17): 2664-2666.

(Continued)

*Primary Examiner* — Nicholas J Plionis
(74) *Attorney, Agent, or Firm* — Morrison & Foerster LLP

(57) ABSTRACT

A surgical light for illuminating a target with light that has a reduced contribution of a portion of the visible spectrum includes a first light source configured to emit light having a first spectrum; a second light source configured to emit light having a second spectrum that does not include the portion of the visible spectrum; and a controller configured to simultaneously activate the first and second light sources for illuminating the target with light that has a reduced contribution of light in the portion of the visible spectrum relative to white light.

28 Claims, 22 Drawing Sheets
(1 of 22 Drawing Sheet(s) Filed in Color)

(56) References Cited

U.S. PATENT DOCUMENTS

| | | | |
|---|---|---|---|
| 2005/0182299 A1* | 8/2005 | D'Amelio | G02B 23/2423 |
| | | | 600/172 |
| 2007/0167701 A1* | 7/2007 | Sherman | A61B 90/35 |
| | | | 600/407 |
| 2007/0179430 A1* | 8/2007 | Smith | A61F 9/00736 |
| | | | 604/20 |
| 2009/0318772 A1 | 12/2009 | Marka et al. | |
| 2010/0203465 A1 | 8/2010 | Bria et al. | |
| 2010/0228089 A1* | 9/2010 | Hoffman | H01S 5/06808 |
| | | | 372/38.07 |
| 2011/0208004 A1 | 8/2011 | Feingold et al. | |
| 2013/0079645 A1* | 3/2013 | Amirana | A61B 1/0638 |
| | | | 600/479 |
| 2013/0147400 A1* | 6/2013 | Van Herpen | F21V 23/04 |
| | | | 362/231 |
| 2015/0362151 A1 | 12/2015 | Van Bommel et al. | |
| 2016/0338795 A1 | 11/2016 | Vayser et al. | |

OTHER PUBLICATIONS

Litorja et al., (Mar. 2007). "Development of Surgical Lighting for Enhanced Color Contrast," Proceedings of SPIE—the International Society for Optical Engineering 6515: 12 pages.

Liu et al., (Jan. 20, 2014). "Investigation of self-adaptive LED surgical lighting based on entropy contrast enhancing method," Optics Communications 319: 133-140.

Murai et al. "Improving color appearance of organ in surgery by optimally designed LED illuminant," World Congress on Medical Physics and Biomedical Engineering, May 26-31, 2012, Beijing, China; pp. 1-4.

Shen et al., (Oct. 2015). "Surgical lighting with contrast enhancement based on spectral reflectance comparison and entropy analysis," Journal of Biomedical Optics 20(10): 105012-1-105012-7.

International Search Report and Written Opinion mailed Feb. 17, 2021, directed to International Application No. PCT/US2020/041010; 15 pages.

Invitation to Pay Additional Fees and, where applicable, Protest Fee mailed Nov. 3, 2020, directed to International Application No. PCT/US2020/041010; 11 pages.

International Preliminary Report on Patentability dated Jan. 11, 2022, directed to International Application No. PCT/US2020/041010; 9 pages.

Notice of Reasons for Refusal dated Jan. 19, 2024, directed to JP Application No. 2022-500919; 12 pages.

Notice of Reasons for Refusal dated May 24, 2024, directed to JP Application No. 2022-500919; 8 pages.

* cited by examiner

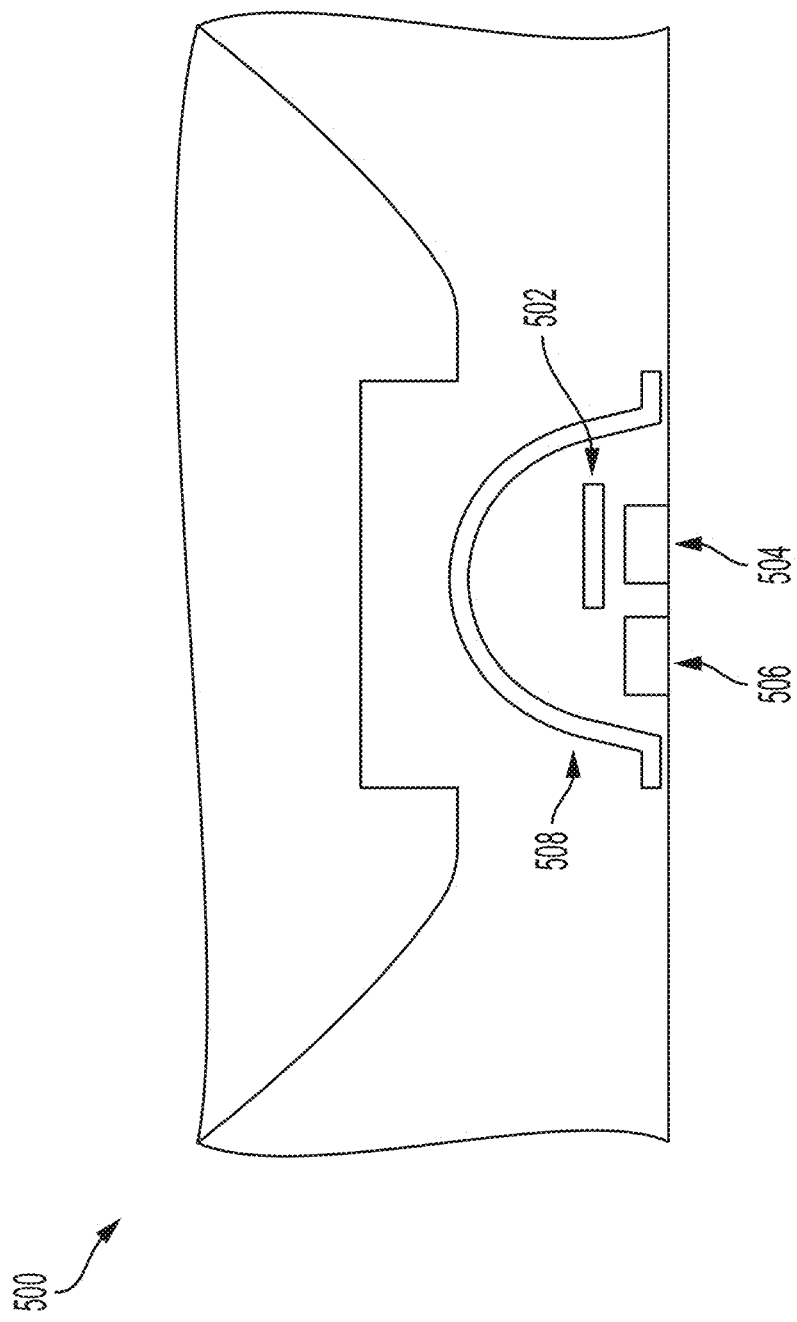

SYSTEMS AND METHODS FOR TARGETED SPECTRAL ILLUMINATION

CROSS-REFERENCE TO RELATED APPLICATIONS

This application claims the benefit of U.S. Provisional Application No. 62/871,586, filed Jul. 8, 2019, the entire contents of which are hereby incorporated by reference herein.

FIELD OF THE INVENTION

The present invention relates to surgical lighting, and in particular, to surgical lighting for open field surgery.

BACKGROUND OF THE INVENTION

Surgical lights are used in operating rooms to provide relatively high intensity light to a target surgical area for illuminating the target surgical area during open field surgery. The target surgical area may be illuminated by the one or more surgical lights for direct observation by the surgeon. Accordingly, many conventional surgical lights are configured to provide light that closely approximates natural light so that tissue in the target appears according to its true colors. During surgery, target tissue is generally perfused with blood and, therefore, the scene may be dominated by the color red. Due to the prevalence of this single color, the contrast between different portions of the tissue may be low such that the surgeon may have difficulty discerning different features of the tissue, or different anatomies, which can lead to eye strain and fatigue.

SUMMARY OF THE INVENTION

According to some embodiments, a surgical light is configured to illuminate a target with a combination of a light having a first spectrum and a light having a second spectrum that lacks a portion of the visible spectrum that is included in the first spectrum. The target tissue can thereby be illuminated with light that has a reduced contribution of the portion of the visible spectrum lacking in the second spectrum. According to some embodiments, the first spectrum, alone, or in combination with the second spectrum can encompass the visible spectrum, which can preserve one or more aspects of the tissue's natural appearance while increasing the contrast between features of the target due to the lower contribution of the portion of the visible spectrum lacking in the second spectrum relative to white light.

In some embodiments, the light having the first spectrum is a white light and the light having the second spectrum lacks at least a portion of red light, which results in the target being illuminated by light having a reduced red contribution relative to white light, which reduces the amount of red light reflected by the target. In an open field surgical procedure, reduced but not eliminated red light reflected from the tissue can preserve the appearance of the tissue while providing increased contrast, reduced glare, and reduced fatigue.

According to some embodiments, a surgical light for illuminating a target with light that has a reduced contribution of a portion of the visible spectrum includes a first light source configured to emit light having a first spectrum that includes the portion of the visible spectrum, a second light source configured to emit light having a second spectrum that does not include the portion of the visible spectrum, and a controller configured to simultaneously activate the first and second light sources for illuminating the target with light that has a reduced contribution of light in the portion of the visible spectrum relative to white light.

In any of these embodiments, the second spectrum can have a narrower spectral range than the first spectrum.

In any of these embodiments, the first spectrum may include the second spectrum.

In any of these embodiments, the first spectrum may have a narrower spectral range than the second spectrum.

In any of these embodiments, the controller can be configured to control the relative amount of light provided by the first and second light sources to adjust the relative contribution of light in the portion of the visible spectrum to the light at the target.

In any of these embodiments, the controller can be configured to adjust the contribution of light in the portion of the visible spectrum while maintaining a constant illuminance at the target.

In any of these embodiments, the portion of the visible spectrum may include at least a portion of the red portion of the visible spectrum.

In any of these embodiments, the second light source may include at least one emitter that is configured to emit light across the second spectrum but not in the portion of the visible spectrum.

In any of these embodiments, the second light source may include at least one light emitter configured to emit light across at least a portion of the first spectrum and at least one filter for filtering out light in the portion of the visible spectrum.

In any of these embodiments, the second light source may include at least one optic and the at least one filter may be disposed on the at least one optic.

In any of these embodiments, the at least one optic may include a lens.

In any of these embodiments, the at least one optic may include a mirror.

In any of these embodiments, the second light source may include at least one optic and the filter may be disposed between the at least one light emitter and the at least one optic.

In any of these embodiments, the first and second light sources may each include at least one solid state white light emitter.

In any of these embodiments, at least one of the first light source and the second light source may include a plurality of white light emitters having different color temperatures.

In any of these embodiments, the first light source may include a plurality of narrow band light emitters having different spectral ranges that collectively emit the light having the first spectrum.

In any of these embodiments, at least one of the first and second light sources may include a plurality of light generating units, each light generating unit including at least one solid state light emitter and at least one optic for manipulating light emitted by the at least one solid state light emitter.

In any of these embodiments, each light generating unit may include a plurality of solid state light emitters.

In any of these embodiments, each light generating unit may include an optical integrator for integrating light from the plurality of solid state light emitters.

In any of these embodiments, at least one light generating unit of the second light source may include a filter disposed on the at least one optic.

In any of these embodiments, the filter may be disposed on an outer surface of the at least one optic that faces away from the at least one solid state light emitter.

In any of these embodiments, the filter may be disposed on an inner surface of the at least one optic that faces toward the at least one solid state light emitter.

In any of these embodiments, light generating units of the first light source may be interspersed with light generating units of the second light source.

In any of these embodiments, light generating units of the first light source may be arranged in a plurality of first arrays, light generating units of the second light source may be arranged in a plurality of second arrays, and the first arrays may alternate with the second arrays.

In any of these embodiments, the surgical light may be configured for suspending above an operating table.

In any of these embodiments, the surgical light may include a housing and the first and second light sources may be mounted in the housing.

In any of these embodiments, the controller may be configured to simultaneously activate the first and second light sources in a first mode and to deactivate the second light source in a second mode for illuminating the target with only the light having the first spectrum.

In any of these embodiments, the surgical light may include a user interface for mode selection by a user.

According to some embodiments, a method for illuminating a target with light that has a reduced contribution of a portion of the visible spectrum includes emitting light having a first spectrum that includes the portion of the visible spectrum from a first light source, simultaneously emitting light having a second spectrum that does not include the portion of the visible spectrum from a second light source, and illuminating the target with light from the first and second light sources simultaneously such that the target is illuminated by light that has a reduced contribution of light in the portion of the visible spectrum relative to white light.

In any of these embodiments, the second spectrum may have a narrower spectral range than the first spectrum.

In any of these embodiments, the first spectrum may include the second spectrum.

In any of these embodiments, the first spectrum may have a narrower spectral range than the second spectrum.

In any of these embodiments, the method may further include deactivating the second light source while the first light source remains activated to illuminate the target with only the light having the first spectrum.

In any of these embodiments, deactivating the second light source may include deactivating the second light source in response to a user selection of a broader spectrum light mode.

In any of these embodiments, the method may further include controlling a relative amount of light emitted by the first and second light sources to adjust a relative contribution of light in the portion of the visible spectrum to the light illuminating the target.

In any of these embodiments, the method may further include adjusting the contribution of light in the portion of the visible spectrum while maintaining a constant illuminance at the target.

In any of these embodiments, the portion of the visible spectrum may include at least a portion of the red portion of the visible spectrum.

In any of these embodiments, the second light source may include at least one emitter that is configured to emit light across the second spectrum but not in the portion of the visible spectrum.

In any of these embodiments, the second light source may include at least one light emitter configured to emit light across at least a portion of the first spectrum and at least one filter for filtering out light in the portion of the visible spectrum.

In any of these embodiments, the second light source may include at least one optic and the at least one filter may be disposed on the at least one optic.

In any of these embodiments, the at least one optic may include a lens.

In any of these embodiments, the at least one optic may include a mirror.

In any of these embodiments, the second light source may include at least one optic and the filter may be disposed between the at least one light emitter and the at least one optic.

In any of these embodiments, the first and second light sources may each include at least one solid state white light emitter.

In any of these embodiments, at least one of the first light source and the second light source includes a plurality of white light emitters having different color temperatures.

In any of these embodiments, the first light source includes a plurality of narrow band light emitters having different spectral ranges that collectively emit the light having the first spectrum.

In any of these embodiments, at least one of the first and second light sources includes a plurality of light generating units, each light generating unit including at least one solid state light emitter and at least one optic for manipulating light emitted by the at least one solid state light emitter.

In any of these embodiments, each light generating unit may include a plurality of solid state light emitters.

In any of these embodiments, each light generating unit may include an optical integrator for integrating light from the plurality of solid state light emitters.

In any of these embodiments, at least one light generating unit of the second light source may include a filter disposed on the at least one optic.

In any of these embodiments, the filter may be disposed on an outer surface of the at least one optic that faces away from the at least one solid state light emitter.

In any of these embodiments, the filter may be disposed on an inner surface of the at least one optic that faces toward the at least one solid state light emitter.

In any of these embodiments, light generating units of the first light source may be interspersed with light generating units of the second light source.

In any of these embodiments, light generating units of the first light source may be arranged in a plurality of first arrays, light generating units of the second light source may be arranged in a plurality of second arrays, and the first arrays may alternate with the second arrays.

In any of these embodiments, the first and second light sources may be suspended above an operating table.

In any of these embodiments, the first and second light sources may be mounted in a housing.

According to some embodiments, a surgical light includes a plurality of light generating units, each light generating unit including: at least one first light emitter that emits light having a first spectrum, at least one second light emitter that emits light having a second spectrum, and at least one optical element that is configured to mix the light from the first and second light emitters such that the light generating unit emits light that is a mixture of the first and second spectrum; and a controller configured to adjust relative intensities of the at least one first light emitter and the at least one second light emitter to adjust the spectrum of light generated by the plurality of light generating units.

In any of these embodiments, the plurality of light generating units can include at least one first light generating unit configured to generate a first illumination pattern at an illumination target and at least one second light generating unit configured to generate a second illumination pattern at the illumination target, wherein, the controller can be further configured to adjust an intensity of light generated by the at least one first light generating unit relative to an intensity of light generated by the at least one second light generating unit to adjust the illumination pattern at the illumination target.

In any of these embodiments, the second illumination pattern can be an annular pattern.

In any of these embodiments, the plurality of light generating units can include at least one third light generating unit configured to generate a third illumination pattern at the illumination target.

In any of these embodiments, the plurality of light generating units can be arranged in a plurality of subassemblies, wherein each subassembly includes at least one first light generating unit and at least one second light generating unit.

In any of these embodiments, the light having the first spectrum can be white light having a first color temperature and the light having the second spectrum can be white light having a second color temperature.

In any of these embodiments, the light can have a curved chassis for mounting the plurality of light generating units so that the light generating units are directed to the same spot.

In any of these embodiments, the at least one optical element can include a Köhler channel.

In any of these embodiments, the at least one optical element can include a micro-lens array.

In any of these embodiments, the Köhler channel can be integrated into a collimating optic.

In any of these embodiments, each light generating unit can include a collimating optic for collimating light from the at least one optical element.

According to some embodiments, a method for illuminating a target with a surgical light includes emitting first light having a first spectrum from at least one first light emitter of the surgical light, emitting second light having a second spectrum from at least one second light emitter of the surgical light, mixing the first and second light by at least one optical element of the surgical light, illuminating the target with the mixed light from the at least one optical element, and adjusting relative intensities of the first and second lights to adjust a spectrum of the mixed light illuminating the target.

In any of these embodiments, the surgical light can include a plurality of light generating units that each includes first and second light emitters, at least one first light generating unit can be configured to generate a first illumination pattern and at least one second light generating unit can be configured to generate a second illumination pattern, and the method can further include adjusting an intensity of light generated by the at least one first light generating unit relative to an intensity of light generated by the at least one second light generating unit to adjust the illumination pattern at the illumination target.

In any of these embodiments, the second illumination pattern can be an annular pattern.

In any of these embodiments, the plurality of light generating units can include at least one third light generating unit configured to generate a third illumination pattern at the illumination target.

In any of these embodiments, the plurality of light generating units can be arranged in a plurality of subassemblies, wherein each subassembly includes at least one first light generating unit and at least one second light generating unit.

In any of these embodiments, the surgical light can include a plurality of light generating units that each comprises first and second light emitters, wherein the surgical light includes a curved chassis for mounting the plurality of light generating units so that the plurality of light generating units are directed to the same spot.

In any of these embodiments, the first light having the first spectrum can be white light having a first color temperature and the second light having the second spectrum can be white light having a second color temperature.

In any of these embodiments, the at least one optical element can include a Köhler channel.

In any of these embodiments, the at least one optical element can include a micro-lens array.

In any of these embodiments, the Köhler channel can be integrated into a collimating optic.

In any of these embodiments, the surgical light can include a plurality of light generating units that each includes first and second light emitters, wherein each light generating unit includes a collimating optic for collimating light from the at least one optical element.

A surgical light includes a plurality of light generating units that include at least one first light generating unit configured to generate a first illumination pattern at an illumination target, and at least one second light generating unit configured to generate a second illumination pattern at the illumination target; and a controller configured to adjust an intensity of light generated by the at least one first light generating unit relative to an intensity of light generated by the at least one second light generating unit to adjust the illumination pattern at the illumination target, wherein the illumination pattern at the illumination target is a combination of the first illumination pattern and the second illumination pattern.

In any of these embodiments, the second illumination pattern can be an annular pattern.

In any of these embodiments, the plurality of light generating units can include at least one third light generating unit configured to generate a third illumination pattern at the illumination target.

In any of these embodiments, the plurality of light generating units can be arranged in a plurality of subassemblies, wherein each subassembly includes at least one first light generating unit and at least one second light generating unit.

In any of these embodiments, the first illumination pattern can be smaller in coverage area than the second illumination pattern and the surgical light can have a smaller number of first light generating units than second light generating units.

According to some embodiments, a method of illuminating a target with a surgical light includes emitting light from at least one first light generating unit of the surgical light, the at least one first light generating unit configured to generate a first illumination pattern at an illumination target; emitting light from at least one second light generating unit of the surgical light, the at least one second light generating unit configured to generate a second illumination pattern at the illumination target; and adjusting an intensity of light generated by the at least one first light generating unit relative to an intensity of light generated by the at least one second light generating unit to adjust an illumination pattern at the illumination target, wherein the illumination pattern at the illumination target is a combination of the first illumination pattern and the second illumination pattern.

In any of these embodiments, the second illumination pattern can be an annular pattern.

In any of these embodiments, the surgical light can include at least one third light generating unit configured to generate a third illumination pattern at the illumination target.

In any of these embodiments, the surgical light can include a plurality of light generating units that are arranged in a plurality of subassemblies, wherein each subassembly includes at least one first light generating unit and at least one second light generating unit.

In any of these embodiments, the first illumination pattern can be smaller in coverage area than the second illumination pattern and the surgical light can have a smaller number of first light generating units than second light generating units.

BRIEF DESCRIPTION OF THE DRAWINGS

The patent or application file contains at least one drawing executed in color. Copies of this patent or patent application publication with color drawings(s) will be provided by the Office upon request and payment of the necessary fee. Features will become apparent to those of ordinary skill in the art by describing in detail exemplary embodiments with reference to the attached drawings in which:

FIG. 5 illustrates a light generating unit that produces both broad spectrum and narrower spectrum light, according to some embodiments;

DETAILED DESCRIPTION OF EXEMPLARY EMBODIMENTS

Figure 1:
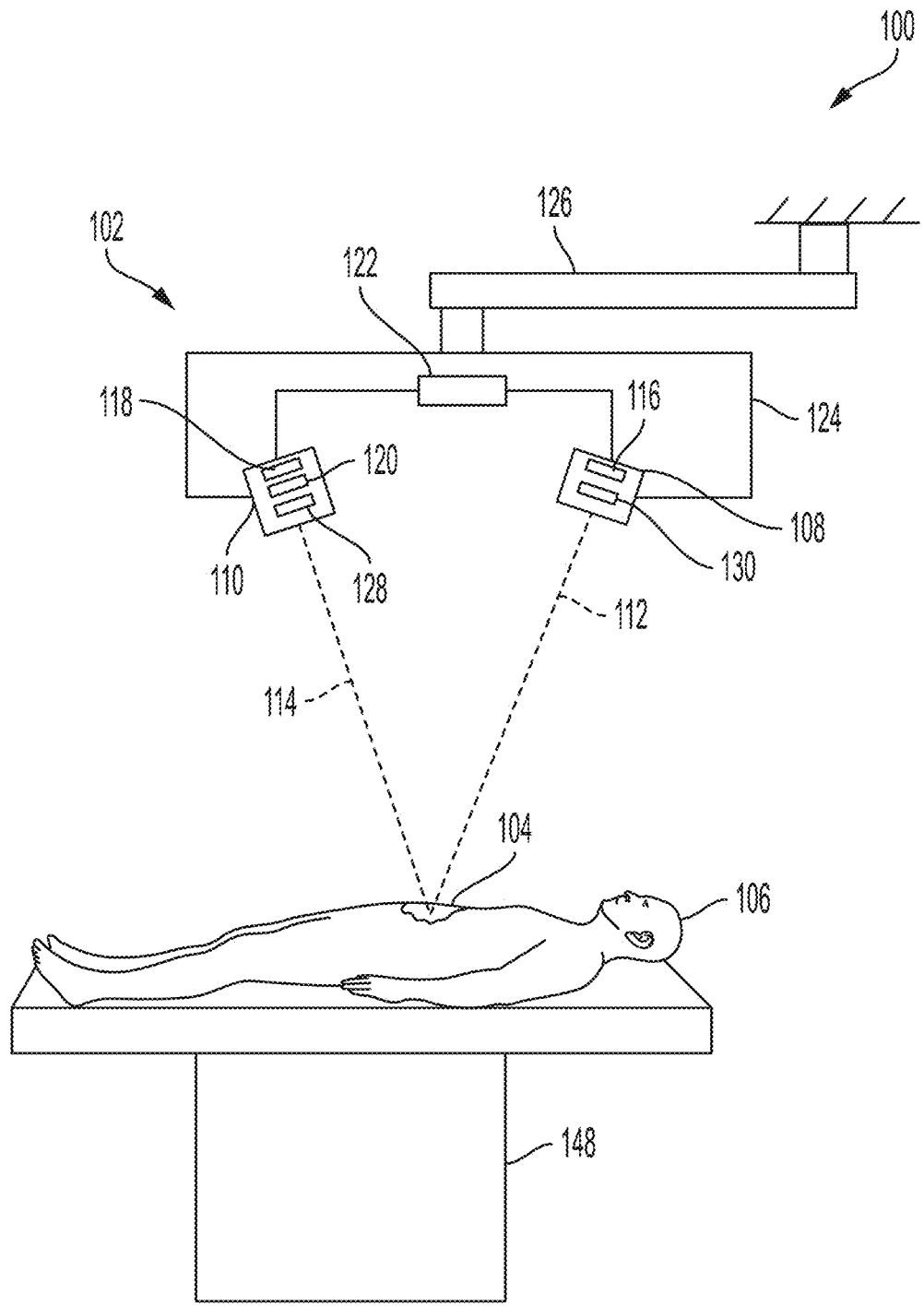
FIG. 1 illustrates a surgical lighting system, according to some embodiments.

Reference will now be made in detail to implementations and embodiments of various aspects and variations of systems and methods described herein. Although several exemplary variations of the systems and methods are described herein, other variations of the systems and methods may include aspects of the systems and methods described herein combined in any suitable manner having combinations of all or some of the aspects described.

Appearance of tissues can be controlled by altering the color of illuminating light, specifically by using reduced-spectrum lighting. However, simply reducing the range of illumination spectrum causes the surgical scene to appear unnatural and can make distinguishing other tissues difficult or impossible. Accordingly, system and methods according to various embodiments mix broad spectrum illumination with illumination that has an attenuated portion of the spectrum relative to the broad spectrum illumination to illuminate a target with light that has a reduced, but not eliminated, contribution of light in the portion of the visible spectrum that is attenuated from the reduced-spectrum illumination.

According to some embodiments, a surgical light includes a first light source for emitting light having a broad spectrum, such as white light. The surgical light includes a second light source for emitting light having a reduced portion of the spectrum relative to the light from the first light source. For example, the second light source may attenuate one or more colors, such as red or one or more of orange, yellow, green, blue, indigo, or violet. According to some embodiments, one or more of these colors is omitted from the light of the second light source altogether. As used herein, the term "attenuated" encompasses omitting altogether; therefore, a portion of the spectrum being attenuated can include the portion of the spectrum being omitted altogether. The first and second light sources may be simultaneously activated so that the target is illuminated by light across the broad spectrum but in which the contribution of the attenuated portion of the spectrum is reduced relative to the light having the broad spectrum. Thus, according to some embodiments, at least some aspects of the natural appearance of the tissue can be preserved while providing one or more advantages of reducing the contribution of the attenuated portion of the spectrum.

For example, in some embodiments, the first light source emits white light and the second light source emits light that lacks at least a portion of the red portion of the visible spectrum. This can be done by filtering the red from light emitted by a white light emitter or can be done by using one or more emitters that do not generate at least a portion of the red portion of the visible spectrum. The first and second light sources are simultaneously activated so that the target is illuminated by a combination of the light from the first and second light sources. The reduced red contribution reduced the amount of red from the target, which in the case of open field surgery, can increase contrast, reduce glare, and or reduce fatigue by reducing the amount of red saturation of the surgical field as perceived by the surgeon's eyes. In other embodiments, different portions of the visible spectrum are attenuated from the second light source, which can, for example, enhance the appearance of various features of the target tissue.

In the following description of the various embodiments, reference is made to the accompanying drawings, in which are shown, by way of illustration, specific embodiments that can be practiced. It is to be understood that other embodiments and examples can be practiced, and changes can be made without departing from the scope of the disclosure.

In addition, it is also to be understood that the singular forms "a," "an," and "the" used in the following description are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

Certain aspects of the present disclosure include process steps and instructions described herein in the form of an algorithm. It should be noted that the process steps and instructions of the present disclosure could be embodied in software, firmware, or hardware and, when embodied in software, could be downloaded to reside on and be operated from different platforms used by a variety of operating systems. Unless specifically stated otherwise as apparent from the following discussion, it is appreciated that, throughout the description, discussions utilizing terms such as "processing," "computing," "calculating," "determining," "displaying," "generating" or the like, refer to the action and processes of a computer system, or similar electronic computing device, that manipulates and transforms data represented as physical (electronic) quantities within the computer system memories or registers or other such information storage, transmission, or display devices.

The present disclosure in some embodiments also relates to a device for performing the operations herein. This device may be specially constructed for the required purposes, or it may comprise a general purpose computer selectively activated or reconfigured by a computer program stored in the computer. Such a computer program may be stored in a non-transitory, computer readable storage medium, such as, but not limited to, any type of disk, including floppy disks, USB flash drives, external hard drives, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The methods, devices, and systems described herein are not inherently related to any particular computer or other apparatus. Various general-purpose systems may also be used with programs in accordance with the teachings herein, or it may prove convenient to construct a more specialized apparatus to perform the required method steps. The required structure for a variety of these systems will appear from the description below. In addition, the present invention is not described with reference to any particular programming language. It will be appreciated that a variety of programming languages may be used to implement the teachings of the present invention as described herein.

FIG. 1 illustrates a schematic representation of a surgical lighting system 100, according to some embodiments. The surgical lighting system 100 includes a surgical light 102 for illuminating target tissue 104 of a subject 106 with a mixture of a light having a first spectrum and a light having a second spectrum. The surgical light 102 includes a first light source 108 and a second light source 110. The first light source 108 emits light 112 having a first spectrum for illuminating the tissue 104 with the light 112. The first spectrum may be a continuous spectrum that has wavelengths of light in a range from a lowest wavelength to a highest wavelength or can be a discontinuous spectrum in which at least some wavelengths between the lowest and highest wavelengths of the light having the first spectrum are not present in the light, such as a spectrum provided by a combination of red, green, and blue emitters. The second light source 110 emits light 114 having a second spectrum for illuminating the tissue 104 with the light 114. The light 114 from the second light source 110 does not have light in a portion of the visible spectrum or the light in the portion of the visible spectrum is attenuated with respect to the relative contribution of that portion of the visible spectrum to the light emitted from the first light source. The first and second light sources 108, 110 can be simultaneously activated so that the first spectrum light 112 and the second spectrum light 114 can combine, either at the target or prior to reaching the target, to illuminate the tissue 104 with a mixture of the first spectrum light 112 and the second spectrum light 114. Thus, the tissue can be illuminated with light across a broad spectrum in which the relative contribution of light in the portion of the visible spectrum lacking from the light 114 emitted by the second light source 110 is reduced with respect to the relative contribution of that portion of visible light relative to white light. In some embodiments, reducing but not eliminating the relative amount of light in the portion of the visible spectrum lacking from the light 114 of second light source 110 and thereby reducing but not eliminating the amount of that light that is reflected from the tissue can preserve the normal appearance of the tissue while providing benefits to the user, such as improved contrast between features of the tissue, reduced fatigue, and/or reduced glare.

In some embodiments, the first spectrum is broader than the second spectrum. For example, the first spectrum may be the visible spectrum. In some embodiments, the first spectrum is narrower than the second spectrum but include the portion of the visible spectrum lacking in the second spectrum. For example, the second spectrum may lack a given color, such as a red or blue, and the first spectrum may include just that color lacking from the second spectrum, such as the red or blue lacking from the second spectrum. According to various embodiments, the first and/or second spectrums includes non-visible light wavelengths, such as ultraviolet light and/or infrared light.

The surgical lighting system 100 includes a controller 122 for controlling the first and second light sources 108, 110. The controller 122 can be a component of the surgical light 102 as shown, or may be operatively coupled to the surgical light 102. The controller 122 controls the first and second light sources 108, 110 such that the first and second light sources 108, 110 emit their respective light 112, 114 simultaneously for providing the first and second spectrum lights to the tissue. In some embodiments, the controller 122 can control the first and second light sources 108, 110 according to different operating modes. For example, in a first mode, both light sources are activated to provide the first and second spectrum lights to the tissue, and in a second mode, the second light source 110 may be deactivated so that the tissue is illuminated with only the first spectrum light. In some embodiments, a third mode may be included in which the first light source 108 is deactivated and the second light source 110 is activated so that the tissue is illuminated with just the second spectrum light.

In some embodiments, the surgical light 102 includes a housing 124 that houses the first and second light sources 108, 110. In some embodiments, the controller 122 is housed within the housing 124. The housing 124 may be mounted to a suspension arm assembly 126 so that the surgical light 102 can be suspended above subject 106, such as above an operating table 148 in an operating room. The suspension arm assembly 126 can attach to the ceiling or other suitable support.

The first light source 108 includes one or more first light emitters 116 that individually or collectively generate light across the first spectrum of the light 112. One or more optical elements 130 may be provided in front of the one or more light emitters 116 to manipulate the light emitted by the one or more light emitters for providing the light to the tissue of the subject, such as by focusing, collimating, collecting, homogenizing, and/or directing the light. The one or more optical elements 130 can include, for example, one or more lenses, mirrors, collimators, and filters.

The second light source 110 includes one or more second light emitters 118 for generating light across at least the narrower spectral range of the narrower spectrum light 114. In some embodiments, the one or more second light emitters 118 are configured for generating light across only the narrower spectral range of the narrower spectrum light 114. In other words, in these embodiments, the one or more second light emitters 118 do not emit light in the portion of the spectrum attenuated from the light 114 emitted by the second light source 110. In other embodiments, one or more filters 120 are provided to filter out the portion of the spectrum (entirely or at least a portion) attenuated from the light 114 emitted by the second light source 110. In these embodiments, the light emitted by the one or more second light emitters includes light in the portion of the spectrum attenuated from the light 114 emitted by the second light source 110 and the one or more filters 120 filter this light out so that the filtered portion of the spectrum is attenuated from the light 114 provided by the second light source 110. In some embodiments, the second light source 110 includes one or more optical elements 128 for manipulating light from the one or more second light emitters 118 for providing to the tissue of the subject. As discussed further below, the one or more filters 120 can be located in any suitable location along the light path from the one or more second light emitters 118, including between the one or more second light emitters 118 and the one or more optical elements 128, downstream of the one or more optical elements 128, and/or directly on one or more surfaces of the one or more optical elements 128.

In some embodiments, the first light source emits light across a narrower spectral range than the second light source. The spectral range of the second light source may lack a portion of the visible spectrum and the first light source may emit light in the portion of the visible spectrum lacking in the light of the second light source. For example, the first light source could emit red-only light and the second light source could emit light that lacks at least a portion of the red portion of the visible spectrum. In some embodiments, the spectral range of the second light source includes all of the visible spectrum except for the portion of the visible spectrum provided by the first light source.

In some embodiments, the first light source include an emitter that generates only the portion of the visible spectrum that is lacking in the light from the second light source. In other embodiments, the first light source includes an emitter that generates light in a portion of the spectrum of the second light source and also includes a filter for filtering out light in the portion of the spectrum of the second light source. For example, the first light source may include a white light emitter and a filter for filtering out all but the portion of the visible spectrum provided by the first light source (e.g., one of red, blue, or green). In some embodiments, the second light source includes a filter for filtering out the portion of the visible spectrum provided by the first light source. For example, the second light source may include a white light emitter and a filter for filtering out the portion of the visible spectrum provided by the first light source (e.g., one of red, blue, or green). In other embodiments, the second light source includes one or more narrower band emitters that do not generate the portion of the visible spectrum provided by the first light source. For example, the second light source may include one or more green and blue emitters and the first light source may include one or more red emitters.

The light emitters of one or more of the first and second light sources, according to various embodiments, can include any type of light emitter, such as incandescent (halogen lamp or a tungsten filament), discharge lamp, solid state, laser, or fluorescent light emitters. In some embodiments, emitters of the first and second light sources include one or more types of solid state light emitters such as one or more types of light-emitting diodes (LEDs), organic light-emitting diodes (OLED), superluminescent diodes (SLD), or polymer light-emitting diodes (PLED). In some embodiments, light emitters of the first and second light sources include narrow spectrum light emitters, such as red, green, and blue LEDs. In some embodiments, light emitters of the first and second light sources include broad spectrum light emitters, such as white light LEDs. In some embodiments, the first and second light sources have the same type or types of emitters. In some embodiments, the first and second light sources can include phosphores. For example, the first light source may use the same type or types of emitters as the second light source. In some embodiments, the first and second light sources both use at least one type of white light LED.

Figure 2:
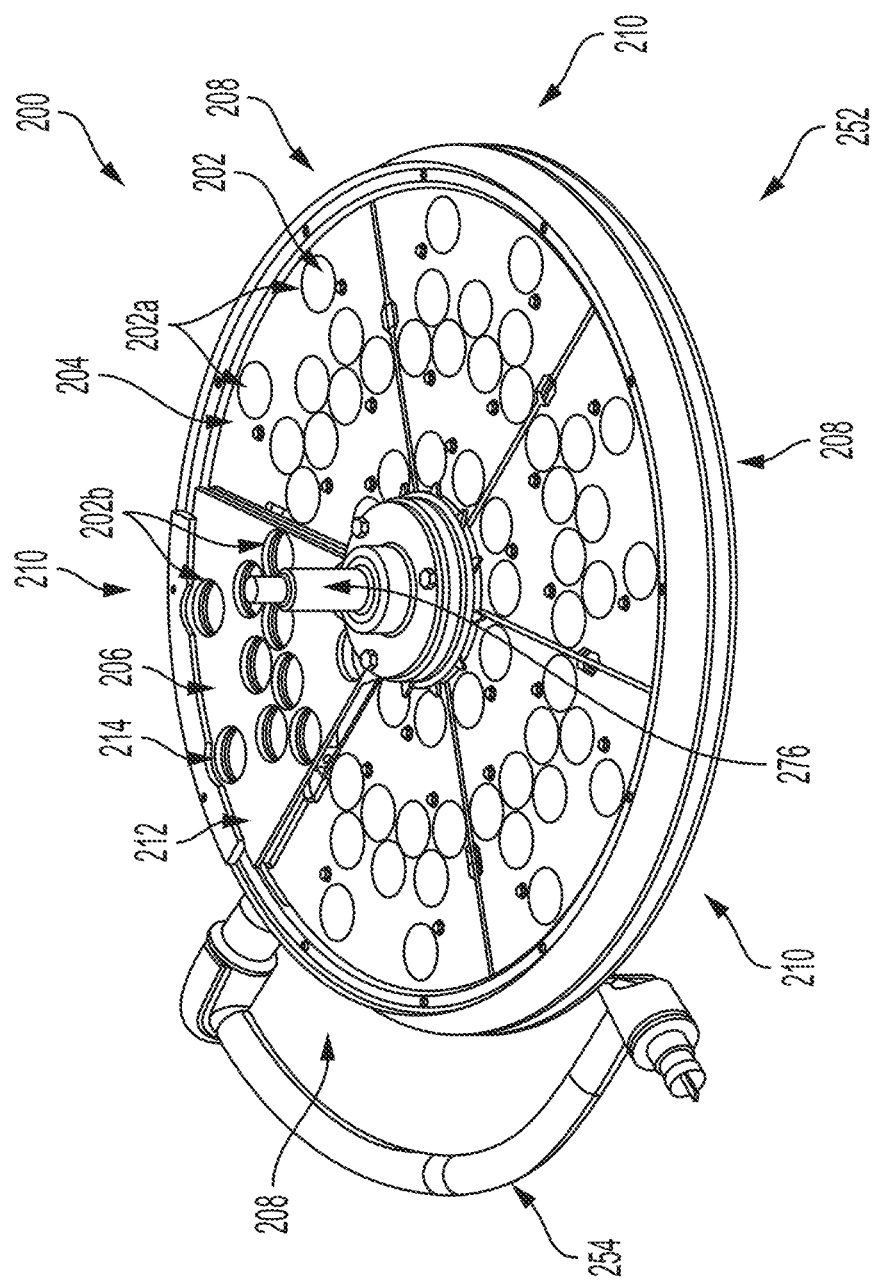
FIG. 2 illustrates a surgical light that includes a plurality of light generating units, according to some embodiments.

First and second light sources, according to various embodiments, can each include a plurality of light generating units that are arranged in a surgical light to provide a suitable illumination pattern at a target. FIG. 2 illustrates an exemplary surgical light 200 that can be used as surgical light 102 of system 100. Surgical light 200 includes a plurality of light generating units 202 that generate light for illuminating the tissue of a subject.

Surgical light 200 is configured to be positioned within a room (e.g., operating room) and to provide increased light to a specific area of the room. While the surgical light 200 can be placed within an operating room, the surgical light 200 can also be placed in any area wherein targeted increased light is desired, such as in a procedure room, an emergency room, a patient room, etc. The surgical light 200 includes a light assembly 252 and an arm 254 for connecting the light assembly 252 to a static or movable structure within the operating room. For example, the arm 254 can be directly connected to a suspension system 126 connected to a wall or ceiling of the operating room, can be connected to a further arm assembly (not shown) or suspension system directly connected to a wall or ceiling of the operating room, or can be directly or indirectly connected to a movable assembly located within the operating room.

In the illustrated example, the arm 254 of the surgical light 200 allows light from the light assembly 252 to be rotated for pointing at a certain area within the operating room (with the suspension system allowing the light assembly 252 to be selectively positioned within the operating room). The surgical light 200 can include a handle assembly 276 for moving the positioning the surgical light 200. In some embodiments, the handle assembly 276 enables a user to alter one or more aspects of the light provided by the surgical light 200, such as turning on, turning off, increasing and decreasing the intensity of the light, increasing and/or decreasing the relative intensities of the first and second light sources, and/or changing the mode of the surgical light according to one or more first/second light source mixing presets. In some embodiments, any of these controls can be provided via one or more mechanical buttons or dials, a touch panel (for example, located on the device or remotely, such as on a wall or other device), speech control, remote control (e.g., RF, IR), and/or via gesture control.

The light generating units 202 include a set of first light generating units 202a that together form a first light source 208 for providing a broad spectrum light to the tissue and a set of second light generating units 202b that together form a second light source 210 for providing a narrower spectrum light to the tissue.

In the illustrated embodiment, the set of first light generating units 202a are arranged in a plurality of first light source arrays 204 and the set of second light generating units 202b are arranged in a plurality of second light source arrays 206. In the illustrated embodiments, there are an equal number of first light source arrays 204 and second light source arrays 206. However, other embodiments can include more first light source arrays than second light source arrays or more second light source arrays than first light source arrays. The first and second light generating units 202a, 202b can be arranged in any suitable fashion. For example, in some embodiments, the light generating units 202a and 202b are interspersed amongst one another, which can include being evenly distributed. For example, in the embodiment illustrated in FIG. 2, light generating units 202a can alternate with light generating units 202b within each ring of light generating units.

Light generating units 202a can be driven together such that when the first light source 208 is activated, each of the light generating units 202a emits light. Similarly, light generating units 202b can be driven together such that when the second light source 210 is activated, each of the light generating units 202b emits light. The first light generating units 202a may be configured to generate the same broad spectrum light and may be arranged to provide a uniform spot of the broad spectrum light at the tissue. The second light generating units 202b may be configured to generate the same narrower spectrum light that omits a portion of the spectrum of the broad spectrum light and may be arranged to provide a uniform spot of the narrower spectrum light at the tissue. The first and second light generating units 202a, and 202b can be arranged with respect to one another so that when both are activated, a uniform spot of mixed light is provided at the tissue. Any suitable number and combination of first and second light generating units 202a, 202b may be provided. In some embodiments more first light generating units 202a are provided than second light generating units 202b. In other embodiments, more second light generating units 202b are provided than first light generating units 202a. In other embodiments, an equal number of first and second light generating units 202a, 202b may be provided.

As described further below, in some embodiments, the second light generating units 202b each include one or more filters for filtering the portion of light that is attenuated from the light emitted by the second light source 210. In some embodiments, a plate 212 that includes a plurality of filters 214 can be positioned on top of the second light generating units 202b, such as on top of each second light source array 206, for filtering out the portion of light.

Figure 3:
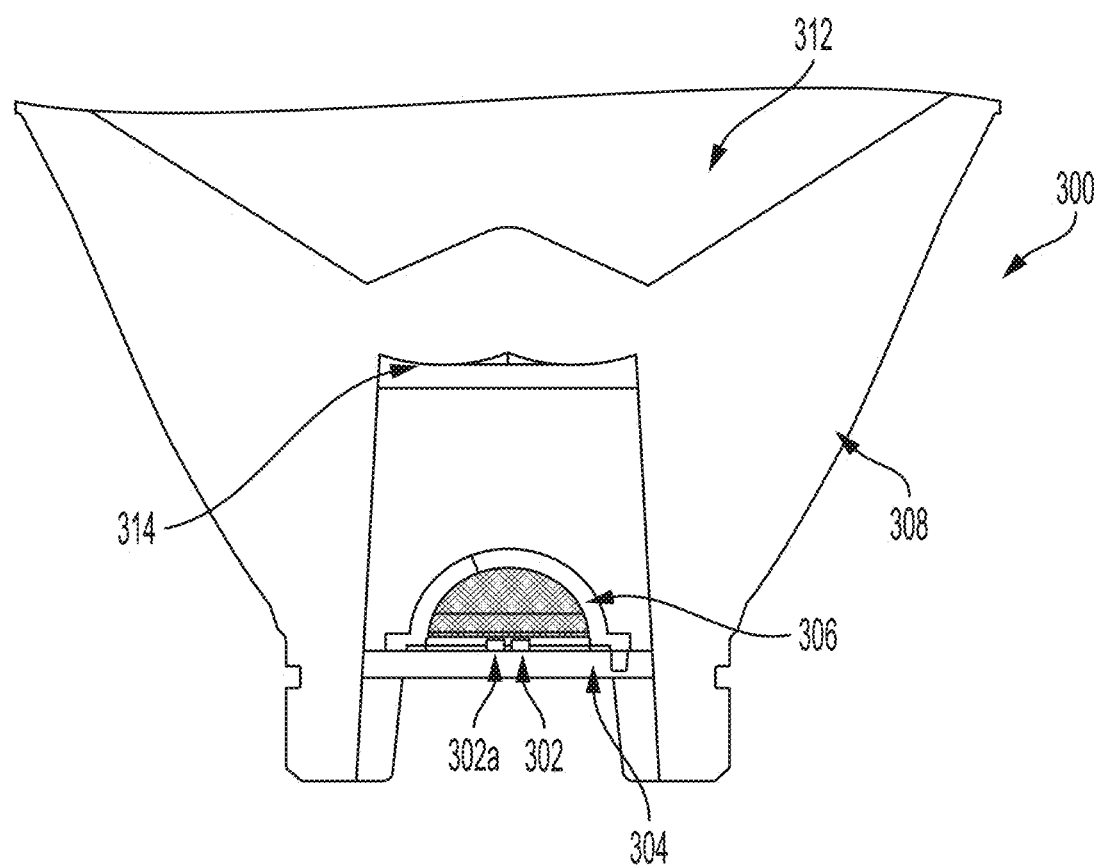
FIG. 3 illustrates a configuration of a light generating unit, according to some embodiments.

FIG. 3 illustrates the configuration of a light generating unit 300, according to some embodiments, that can be used in a surgical light, such as for the first light source 108 and/or a second light source 110 of surgical light 102 or the light generating units 202 of surgical light 200. Light generating unit 300 includes at least one solid state light emitter 302 for generating light. The at least one emitter 302 is mounted on a substrate 304 that includes at least a portion of the circuitry for driving the at least one emitter 302. In some embodiments, a first optic element 306, such as a micro-lens array or other type of optical integrator, is positioned over the at least one emitter 302 for integrating (e.g., homogenizing) light emitted by the at least one emitter 302.

A second optic element 308 may be positioned above the first optic element 306 for directing light from the first optic element 306, which can include collimating and/or focusing the light from the first optic element 306. In some embodiments, the second optic element 308 is a total internal reflection (TIR) element.

In some embodiments, the at least one emitter 302 generates broad spectrum light. In some embodiments, a plurality of emitters 302 are provided with each emitter generating light in a different band such that the collective light from the plurality of emitters 302 together providing a broad spectrum light. In other embodiments, each emitter 302 generates broad spectrum light. In some embodiments, multiple emitters that generate the same broad spectrum light are provided. In some embodiments, multiple emitters that generate different broad spectrum light are provided. For example, emitter 302 may generate a white light having a first color temperature and a second emitter 302a may generate white light having a second color temperature that is different than the first.

According to some embodiments, light generating unit 300 can be configured for use in a first light source, such as first light source 208, for providing broad spectrum light to the tissue. For example, the at least one emitter 302 can include one or more broad spectrum emitters, such as one or more white light emitters. In other embodiments, the at least one emitter 302 can be a plurality of narrower spectrum emitters that combine to provide the broad spectrum light. For example, the at least one emitter 302 can include red, green, and blue LEDs.

According to some embodiments, light generating unit 300 can be configured for use in a second light source, such as second light source 210, for providing narrower spectrum light in which a portion of the broad spectrum is attenuated. In some embodiments, the light generating unit 300 is configured for use in the second light source by including one or more emitters 302 that emit light in a reduced spectrum that does not include the portion of the spectrum to be attenuated. For example, in embodiments in which the red portion of the spectrum is omitted altogether from light emitted by the second light source, the one or more emitters 302 can include blue and green LEDs but no red LEDs.

Figure 4B:
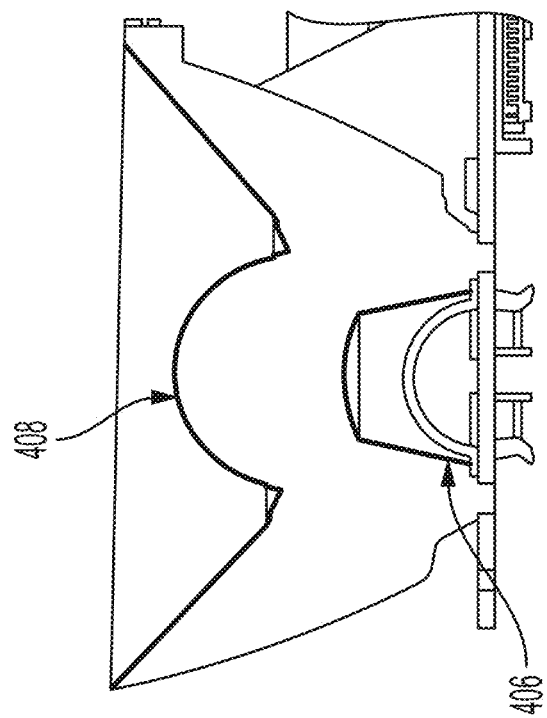
FIGS. 4A and 4B illustrate various locations for positioning a filter on the light generating unit of FIG. 3.
Figure 4A:
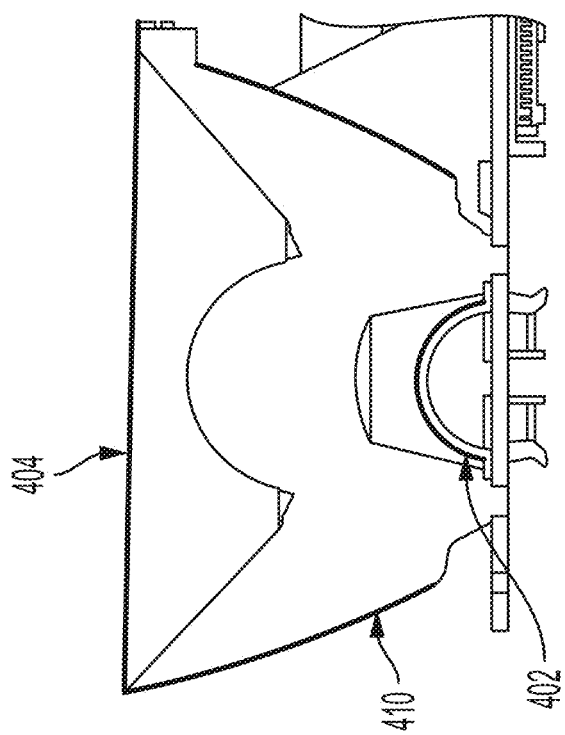

In some embodiments, light generating unit 300 can be configured for providing a reduced spectrum light by including one or more filters in the light path downstream of the one or more emitters 302. FIGS. 4A and 4B illustrate various locations for positioning a filter on the light generating unit 300 to configure the light generating unit to generate narrower band light. A filter 402 can be provided on the first optic element 306, such as by coating the inner and/or outer surface of the first optic element 306. A filter 404 can be provided on a third optic element that is positioned over an outer surface 312 of the second optic element 308. The third optic element can be, for example, a lens or a glass covering. A filter 408 can be provided directly on the outer surface 312. A filter 406 can be provided on an inner surface 314 of the second optic element 308—the surface that faces the first optic element 306. A filter 410 can be provided on the outer conical surface of the second optic element 308. Various embodiments can include one or more of these filters.

FIG. 5 illustrates an embodiment of a light generating unit that produces both broader spectrum light and narrower spectrum light and can be used in various embodiments of any of the systems described herein, including in surgical light 102 and surgical light 200. Light generating unit 500 is configured similarly to light generating unit 300 except that a filter 502 is positioned above a first emitter 504 while no filter is provided above the second emitter 506. The first and second emitters 504, 506 can be configured to generate broad spectrum light. The filter 502 filters out the portion of the broad spectrum that is attenuated from the light of the second light source. The first optic element 508 integrates (e.g., homogenizes) the light from the two emitters such that light emitted by the light generating unit 500 is a mixture of the broad spectrum light and the narrower spectrum light. In this embodiment, the first light source can include first emitters 504 from multiple light generating units 500 and the second light source can include second emitters 506 from the multiple light generating units 500. The group of first emitters can be activated as a group and the collection of second emitters can be activated as a group such that broad spectrum light can be provided from the multiple light generating units 500, narrower spectrum light can be provided from the multiple light generating units 500, and/or a mixture of the broad spectrum and narrower spectrum light can be provided from the multiple light generating units.

Figure 6:
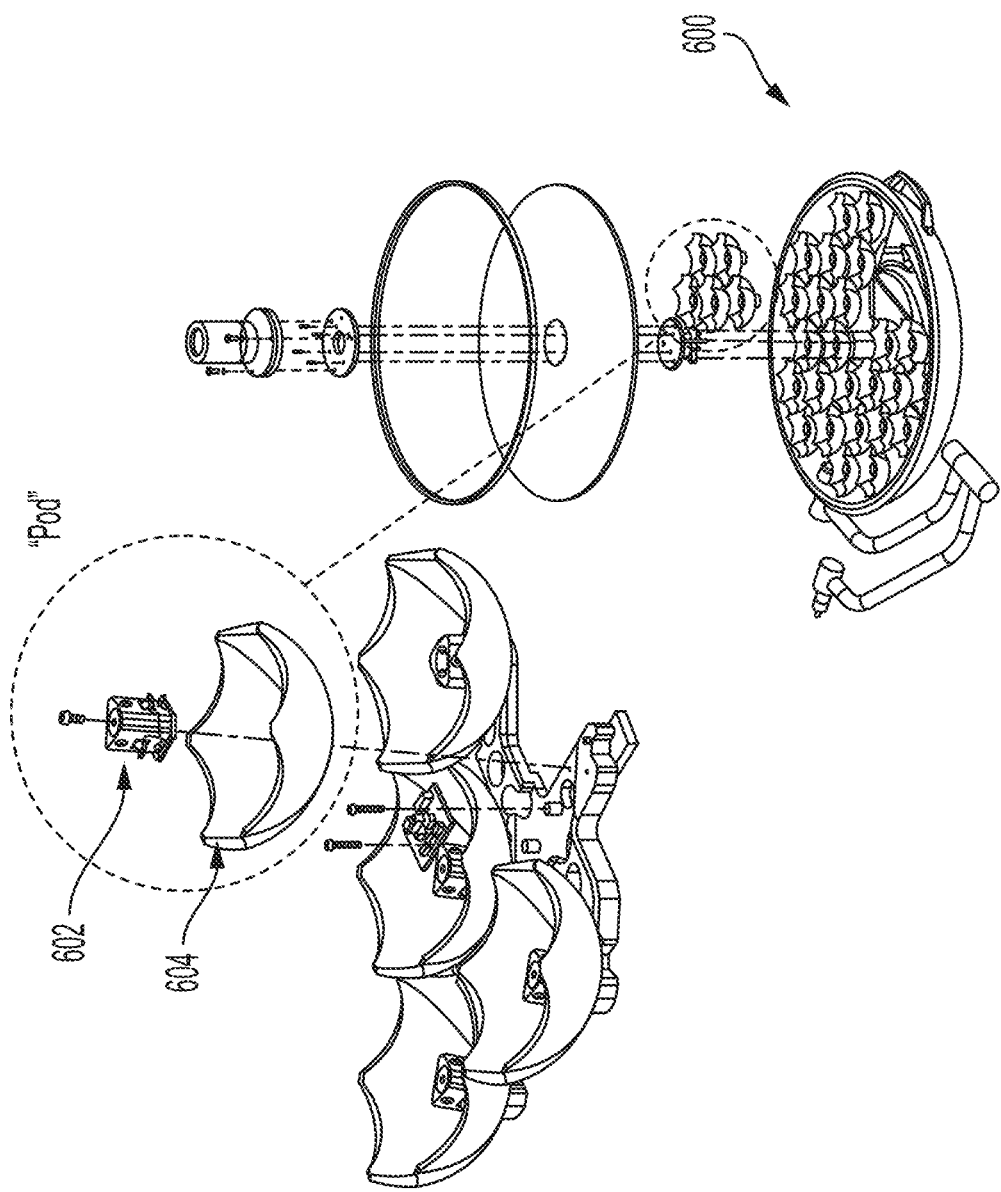
FIG. 6 illustrates a configuration of a light generating unit that includes a parabolic mirror, according to some embodiments.

FIG. 6 illustrates a light generating unit 600, according to some embodiments. Light generating unit 600 includes a light emitter assembly 602 that can include a plurality of light emitters, such as one or more LEDs, that generate broad spectrum light. The light emitter assembly 602 is positioned in the center of an approximately parabolic mirror 604, which directs the light from the emitters into a beam. Light generating unit 600 can be configured for emitting narrower band light by including one or more filters in the light pathway. For example, the mirror 604 can be coated with a filter material for filtering out the portion of the broad spectrum that is to be attenuated. In other embodiments, a filter can be positioned between the emitters of the light emitter assembly 602 and the mirror 604.

Figure 7:
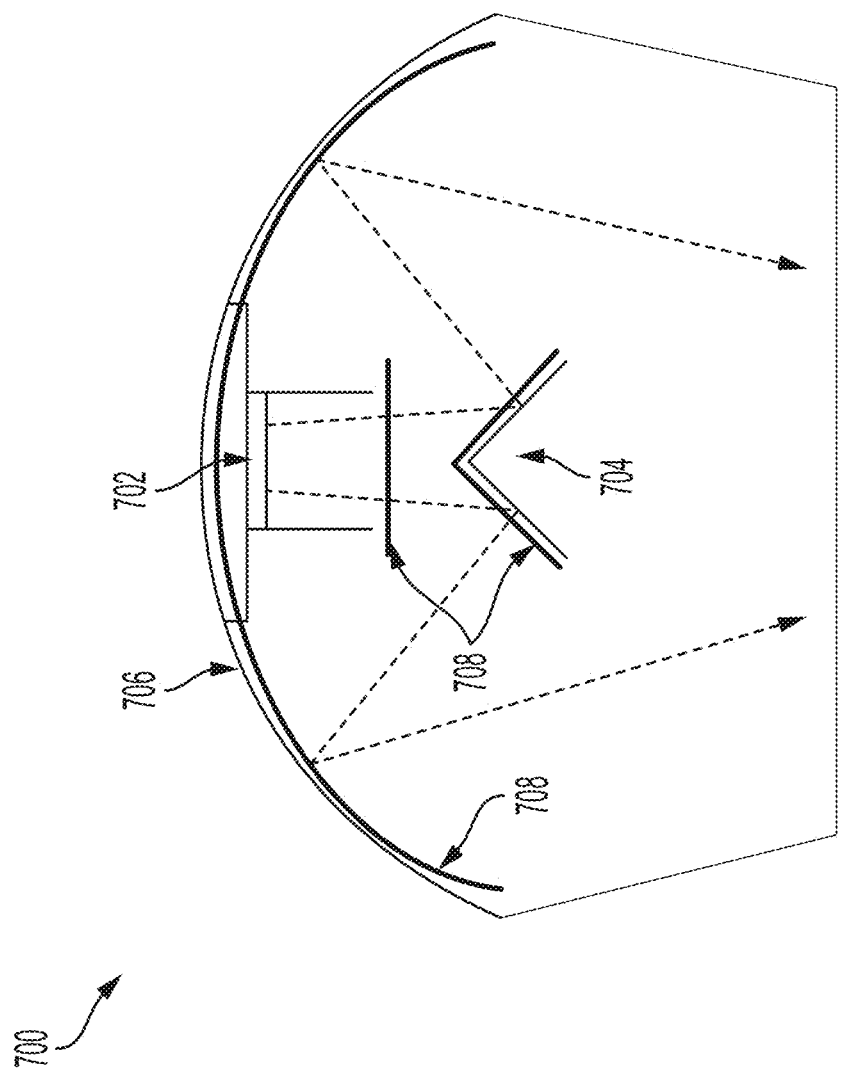
FIG. 7 illustrates a light generating unit that includes multiple mirrors, according to some embodiments.

FIG. 7 illustrates a light generating unit 700, according to some embodiments. Light generating unit 700 includes a light emitter 702 that emits light toward a central reflector 704. The central reflector 704 reflects light from the emitter 702 toward a parabolic reflector 706, which directs the light outwardly from the light generating unit 700. Light generating unit 700 can be configured for generating narrower spectrum light by including a broad spectrum emitter 702 and providing one or more filters 708 in the optical path. The one or more filters 708 can be positioned between the emitter 702 and the central reflector 704, directly on the central reflector 704, or directly on the parabolic reflector 706. The light generating unit 700 can be configured for emitting broad spectrum light by including a broad spectrum emitter and omitting the one or more filters 708. As discussed above, a surgical light can be configured for providing a combined broad band and narrower band illumination by including at least one light generating unit 700 configured with a filter 708 for providing narrower spectrum illumination and at least one light generating unit 700 configured without a filter 708 for providing broad spectrum illumination. The relative numbers of broad band and narrower band light generating units and/or the respective manner in which they are driven can be tailored for the desired mix of narrower band and broad band illumination.

Figure 8:
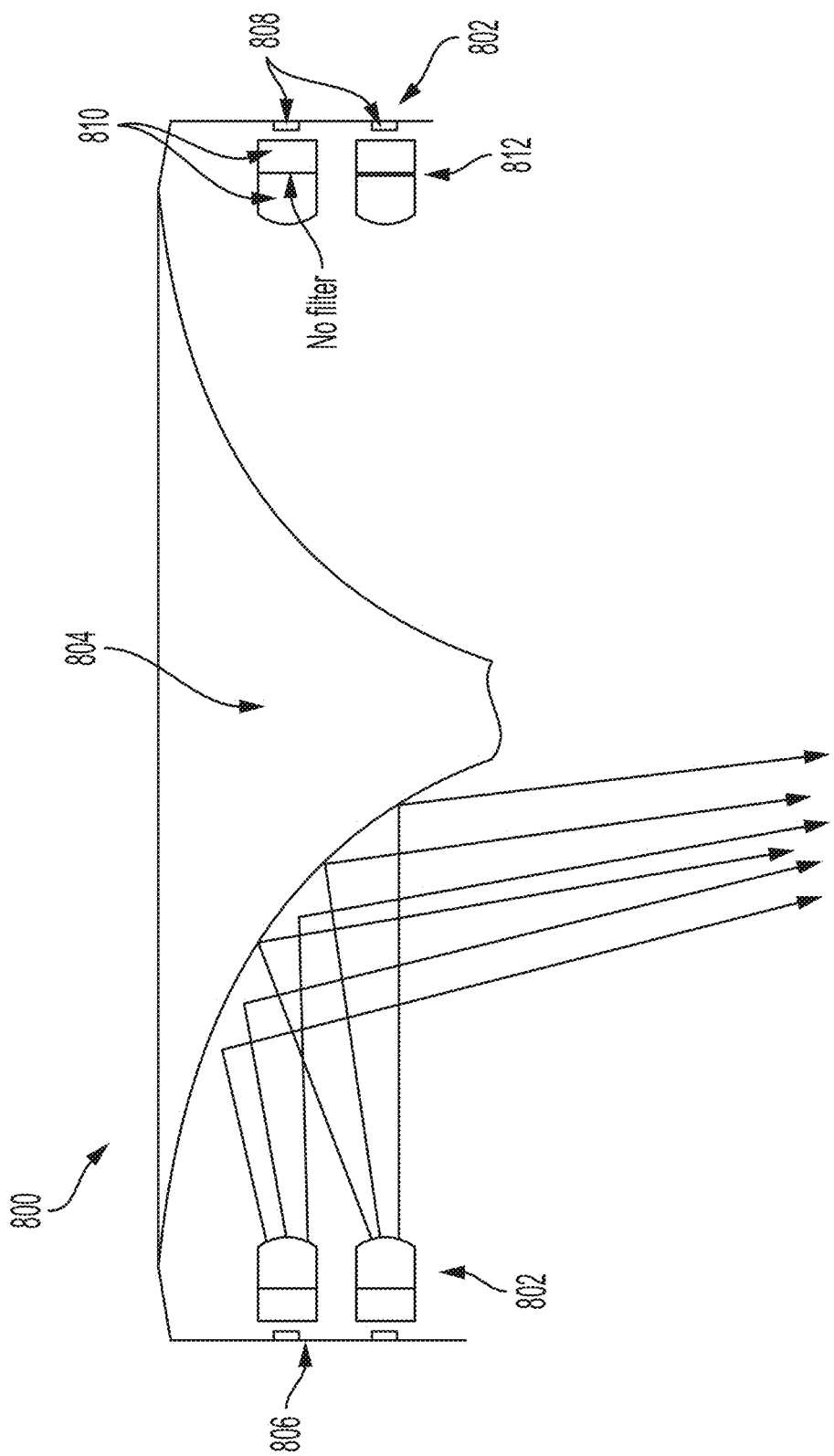
FIG. 8 illustrates a surgical light having a plurality of light generating units that emit light toward a central mirror unit, according to some embodiments.

FIG. 8 illustrates a surgical light 800 in which a plurality of light generating units 802 are arranged along a wall 806 and are directed inwardly to emit light toward a central mirror unit 804 that reflects the light from the light generating units 802 outward from the center of the surgical light 800. Each light generating unit 802 can include one or more light emitters 808 and one or more optical elements 810 (which may include multiple different types of optical elements) for manipulating the light from the one or more light emitters 808. A portion of the light generating units 802 can be configured for emitting the narrower band light by including one or more filters 812 at one or more locations long the optical path. For example, a filter may be positioned between the emitter 808 and optical element 810, between two optical elements 810, or downstream of the optical elements 810.

As discussed above, a surgical light can include a first light source that emits light having a first spectrum and a second light source that emits light having a second spectrum in which a light in a portion of the visible spectrum is reduced or lacking altogether. The second light source can be configured in any suitable manner to emit light having a desired spectral range. For example, in some embodiments, the light from the second light source can lack light in at least a portion of the red spectrum. In other embodiments, a blue portion or a green portion of the spectrum can be lacking from the light from the second light source. In some embodiments, multiple distinct portions of the visible spectrum can be reduced or omitted from the light from the second light source. These are merely examples and a person of skill in the art will understand that a second light source can be configured to provide any spectrum of light via the use of suitable filters and/or light emitters.

According to various embodiments, one or more filters are included in the second light source for filtering out light in a narrow band. The one or more filters can include absorptive filters and/or interference/dichroic filters. One or more filters can be disposed directly on one or more optics, such as a by coating one or more surfaces of a lens or mirror with a dichroic filter coating or an absorptive dye coating.

According to some embodiments, one or more filters of the second light source can filter out light in a relatively narrow portion of the visible spectrum. For example, one or more filters can be provided for filtering out at least a portion of red light such that light provided by the second light source lacks the at least a portion of red light. The second light source can be configured so that the at least a portion of red light is filtered from white light such that the spectrum of light provided by the second light source includes the other colors of visible light, lacking only the at least a portion of the red light.

According to various embodiments, a second light source can be configured to omit any other portion of the visible spectrum, such as orange light, yellow light, green light, cyan light, blue light, or violet light, or any combination of these colors. In some embodiments, the second light source is configured for omitting a single color, such as any one of red, orange, green, cyan, blue, or violet. In other embodiments, the second light source is configured for omitting more than one color, such as by filtering out at least a portion of red light and at least a portion of orange light.

In some embodiments, the second light source is configured to provide light across the visible light spectrum except for a narrow band that includes at least a portion of wavelengths from 400-450 nm, at least a portion of wavelengths from 450-490 nm, at least a portion of wavelengths from 490-520 nm, at least a portion of wavelengths from 520-560 nm, at least a portion of wavelengths from 560-590 nm, at least a portion of wavelengths from 590-635 nm, or at least a portion of wavelengths from 635-700 nm.

In some embodiments, the first light source is configured to provide light across the visible spectrum, such as white light. In some embodiments, the first light source is configured to provide light across only a portion of the visible spectrum. In some embodiments, the first light source is configured to provide light in only the portion of the visible spectrum lacking in the second light source. For example, in some embodiments, the second light source lacks red light and the first light source emits only red light, or the second light source lacks blue light and the first light source emits only blue light.

In some embodiments, the portion of the visible light spectrum attenuated from the light of the second light source, such as via filtering, may be less than the portion of the visible spectrum that is included in the light emitted by the second light source. According to various embodiments, the portion of the visible light spectrum that is attenuated from the light of the second light source is less than 50% of the visible light spectrum, less than 40% of the visible light spectrum, less than 30% of the visible light spectrum, less than 10% of the visible light spectrum, or less than 5% of the visible light spectrum. According to some embodiments, the portion of the visible light spectrum attenuated from the light of the second light source can be filtered from light emitted by emitters using one or more bandpass filters, lowpass filters, highpass filters, and/or notch filters.

Figure 9:
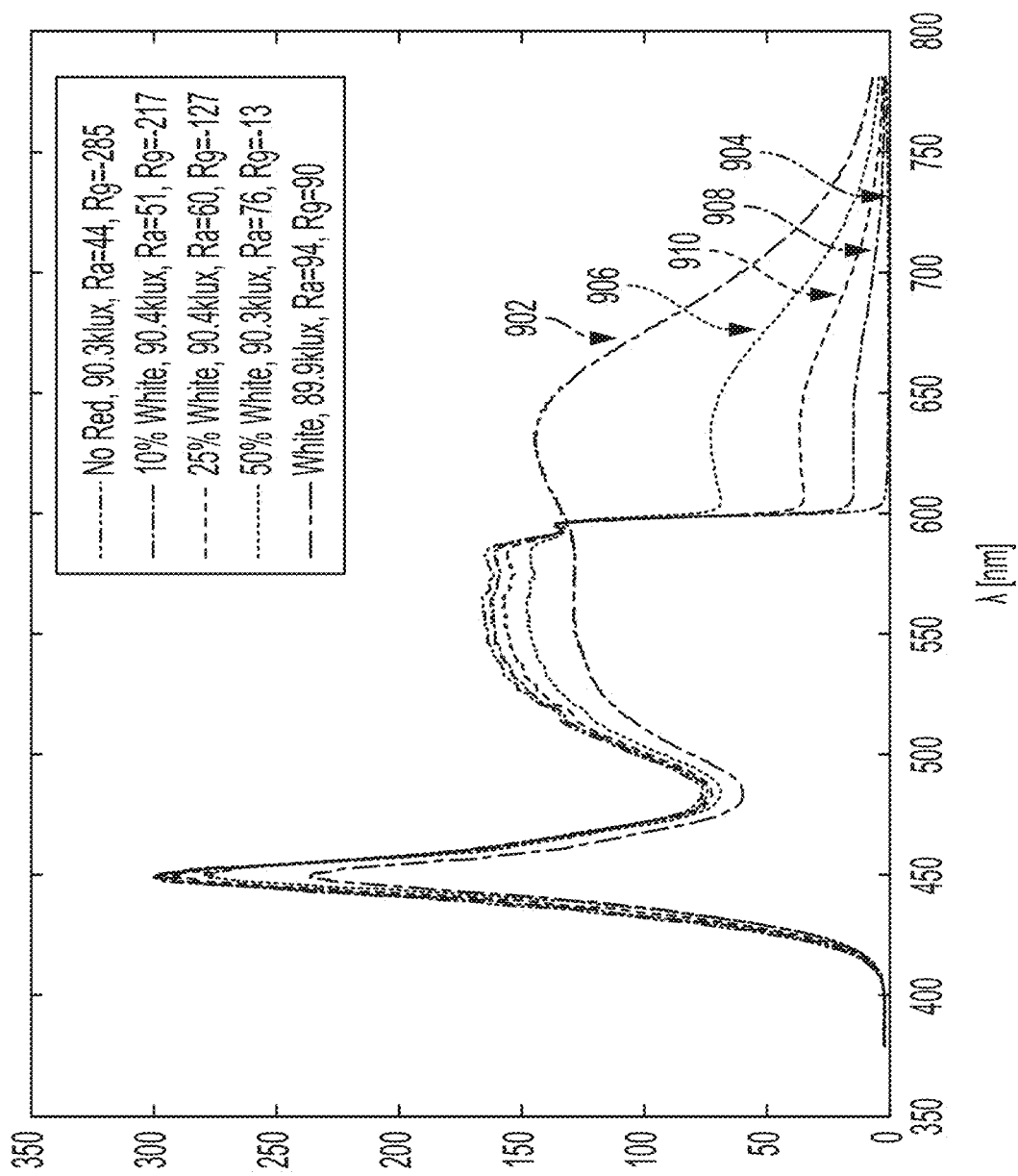
FIG. 9 illustrates the spectra of light provided to a target by a surgical light operating in different modes, according to various embodiments.

Surgical lights, according to various embodiments, can include first and second light sources that are configured and controlled to provide any desired combination of broad spectrum and narrower spectrum light. FIG. 9 illustrates the spectra of light provided to a target by a surgical light operating in different modes, according to various embodiments. Curve 902 shows the spectrum of a first mode in which only the first light source is activated. As illustrated, light from the first light source is broad spectrum white light that includes all wavelengths of light in the range from below 425 nm to above 700 nm. Curve 904 shows the spectrum of a second mode in which only the second light source is activated. The second light source emits light in a narrower spectrum that omits light having wavelengths above about 600 nm, which includes the red portion of the visible spectrum. Thus, the spectrum of light emitted by the second light source is narrower than the spectrum of the first light source. The light emitted by the second light source includes a continuous range of wavelengths from below 425 nm to about 600 nm.

In the illustrated embodiment, the second light source includes one or more filters that filter out light having wavelengths above a filter threshold, which in the illustrated embodiment is about 600 nm. One or more emitters of the second light source are the same (i.e., same type of emitter) as one or more emitters of the first light source, and therefore, the spectrum of light provided by the second light source that is below the filtering threshold of about 600 nm is substantially the same as that provided of the first light source as can be seen by comparing the shape of curve 904 to curve 902 below about 600 nm. For example, both spectra include a peak at about 450 nm and a dip at about 480 nm.

In the illustrated embodiment, the second light source is configured and/or controlled so that the illuminance at the target provided in the second mode is the same as the illuminance at the target provided in the first mode. Therefore, the intensity of light in the portion of the spectrum below the filter threshold is greater than in the corresponding portion of the first light source mode to make up for the lack of light in the omitted portion of the threshold. As shown in the legend, the illuminance of both the first light source mode and the second light source mode is about 90 klux.

Curves 906, 908, and 910 show the emission spectra resulting from three different combinations of first and second light source emissions, according to three different operating modes. For example, curve 906 corresponds to a third mode in which 50% of the light at the target is provided by the first light source—the broad band light source—with the other 50% being provided by the second light source—the narrower band light source. Since the second light source does not provide light above the filter threshold of about 600 nm, the light above 600 nm is provided only by the first light source and, thus, is about half the intensity of the first light source mode (see curve 902). In the illustrated embodiment, the first and second light sources are controlled to provide substantially the same illuminance as in the first and second modes—about 90 klux. Therefore, the intensity of light in the portion of the spectrum below the filter threshold is greater than the corresponding portion of the first mode but less than the corresponding portion of the second mode.

Curve 908 shows the emission spectrum for a fourth mode in which 10% of the light is provided by the first light source, with the remaining 90% being provided by the second light source. Curve 910 shows the emission spectrum for a fifth mode in which 25% of the light is provided by the first light source, with the remaining 75% being provided by the second light source. In both the fourth and fifth modes, the first and second light sources are controlled so that the illuminance at the target is the same as in the first mode—about 90 klux.

Figure 10:
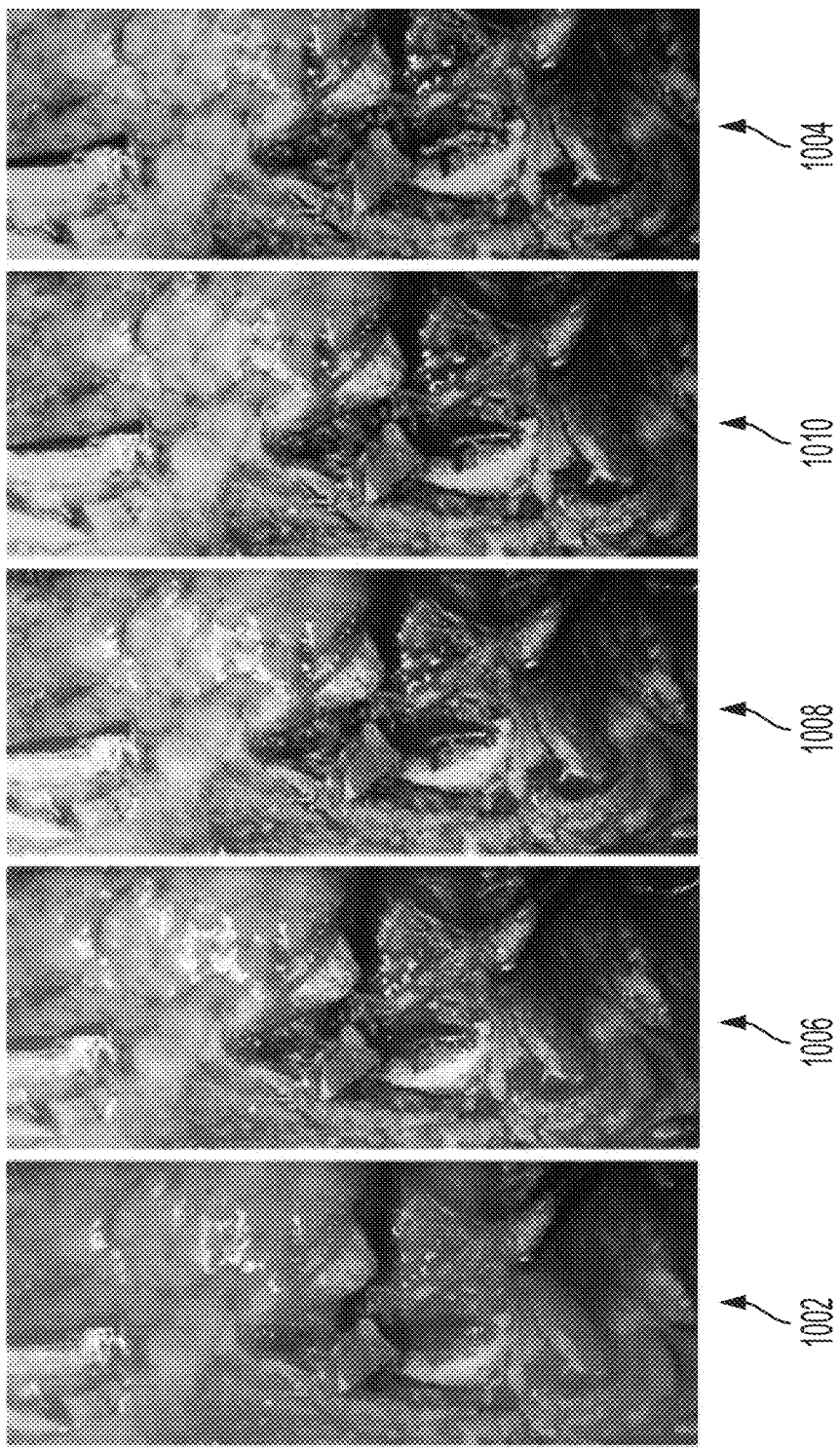
FIG. 10 provides images of tissue of a subject illuminated with light according to the modes of FIG. 9; according to some embodiments.

FIG. 10 provides images of tissue of a subject illuminated with light according to the five modes discussed above with respect to FIG. 9. Image 1002 shows the tissue illuminated with the first light source only, according to the first mode represented by curve 902 of FIG. 9. Due to the amount of blood present in the target tissue, the image includes a substantial amount of red with little contrast between different portions of the tissue.

Image 1004 shows the tissue illuminated with just the second light source in the second mode represented by curve 904 of FIG. 9. Because the second light source filters out red light, image 1004 has substantially no red since there is no red in the illumination light to be reflected by the tissue. Relative to the image 1002 of the first mode, image 1010 of the second mode has improved contrast between different portions of the tissue.

Image 1006 shows the tissue illuminated with the 50% white light of mode three. Image 1008 shows the tissue illuminated with the 25% white light of mode four, and image 1010 shows the tissue illuminated with the 10% white light of mode five. Comparing the images from left to right, it can be seen that as the relative contribution of red light decreases, contrast generally increases but the appearance of the tissue becomes more unnatural. The relative amounts of white light and no-red light can be adjusted to achieve a balance of contrast and natural appearance that according to the preferences of the surgeon.

Figure 11:
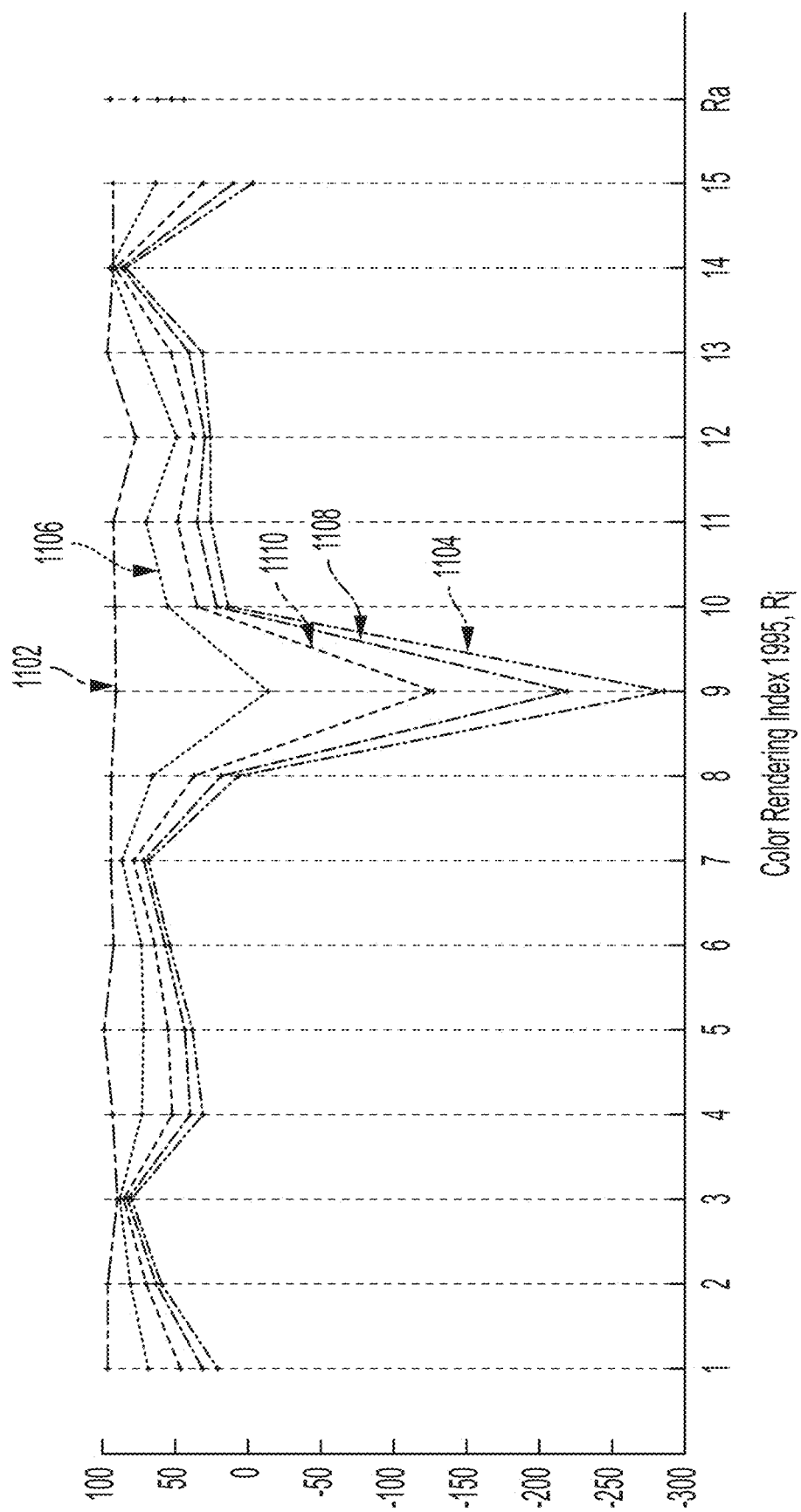
FIG. 11 is a chart of the color rendering indexes for the five light modes of FIG. 9, according to some embodiments.

FIG. 11 is a chart of the color rendering index (CRI), according to CIE 013.3 "Method of measuring and specifying colour rendering properties of light sources," across the 15 test colors and the average CRI (Ra) for the five light modes of FIG. 9. The CRI for the first light source—the white light source—is provided by line 1102. The R9 (red) CRI for the first light source is high—above 90. The R9 CRI for the second light source—the red omitted light source—is, of course, very low as shown by line 1104. As shown by lines 1106, 1108, and 1110, the R9 CRIs for the three mixing modes are also very low due to low contribution of red relative to white light.

Figure 12:
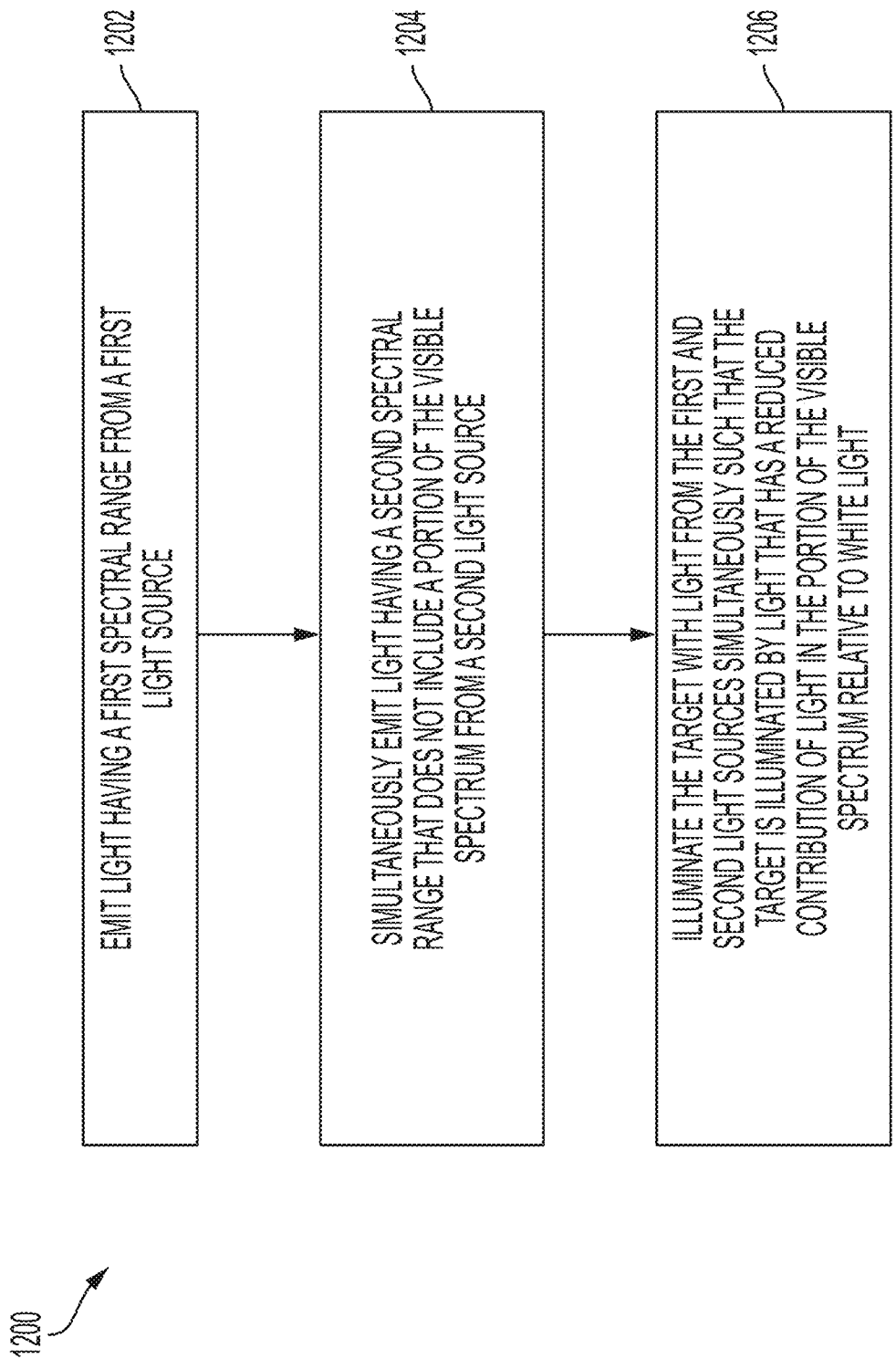
FIG. 12 is a block diagram of a method 1200 for illuminating a target, according to some embodiments.

FIG. 12 is a block diagram of a method 1200 for illuminating a target with light that has a reduced contribution of a portion of the visible spectrum, according to some embodiments. Method 1200 can be performed by a surgical light, such as surgical light 102 of FIG. 1. At step 1202, light having a first spectrum that includes the portion of the visible spectrum being reduced at the target is emitted by a first light source. The first light source may be a component of a surgical light, such as first light source 108 of surgical light 102. The first spectrum can include the portion of the visible spectrum whose contribution at the target is reduced relative to white light. The first spectrum may encompass substantially all of the visible spectrum or only a portion of the visible spectrum. The first spectrum may be a continuous spectral range in which all wavelengths of light within the upper and lower thresholds of the first spectral range are emitted or may be a discontinuous spectrum that includes discrete portions of the visible spectrum. The light emitted by the first light source may be generated by a white light source, such as a solid state white light emitter, may be generated by a combination of narrower-band emitters that together substantially simulate white light, such as red, green, and blue emitters, or may be generated by one or more narrower-band emitters that generate a spectral range that is narrower than white light, including, for example, just red light, just blue light, just green light, just a portion of any of these, etc. In some embodiments, the first spectrum encompasses red, green, and blue portions of the visible spectrum.

At step 1204, light having a second spectrum that does not include the portion of the visible spectrum that is reduced relative to white light is emitted from a second light source simultaneously with the light of the first light source. The second light source can be a component of the surgical light that includes the first light source, such as a second light source 110 of surgical light 102. In some embodiments, the light having the second spectrum is emitted by filtering out light in the portion of the visible spectrum. In other embodiments, the light having the second spectrum is emitted by generating light from one or more emitters that, together, do not generate light in the portion of the visible spectrum. In some embodiments, the second spectrum is narrower than the first spectrum. For example, the first spectrum may encompass the visible spectrum and the second spectrum may encompass the visible spectrum less the portion of the visible spectrum being reduced at the target. In some embodiments, the second spectrum is broader than the first spectrum. For example, the second spectrum may encompass the visible spectrum except for the portion of the visible spectrum being reduced at the target and the first spectrum may include just the portion of the visible spectrum being reduced at the target. In some embodiments, the portion of the visible spectrum being reduced at the target is one specific color of light (e.g., red light, green light, blue light, etc.) and the first spectrum encompasses just the specific color (e.g., red light, green light, or blue light) and the second spectrum encompasses the portions of the visible spectrum other than the specific color (e.g., green and blue light, red and green light, or red and blue light).

At step 1206, a target, such as a target tissue of a subject, is illuminated with light from the first and second light sources such that the target is illuminated by light that has a reduced contribution of light in the portion of the visible spectrum omitted from the light of the second light source relative to white light and included in the light of the first light source. As such, a combination of light from the first light source and light from the second light source illuminates the target. In some embodiments, the first light source alone or the combination of first and second light sources illuminate the target with light across a broad spectrum (e.g., white light), and therefore, the target is illuminated with light across the broad spectrum. However, because the light illuminating the target includes light from the second light source, which lacks or has a reduced contribution of the portion of the visible spectrum being reduced at the target, the contribution of the portion of the visible spectrum omitted from the light emitted by the second light source to the light illuminating the target can be reduced relative to white light. According to various embodiments, the light from the first light source and the light from the second light source can be mixed at the target or in the surgical light itself so that the light is mixed prior to reaching the target.

According to some embodiments, the first and second light sources can be controlled to adjust the mixture of first and second spectrum lights that illuminate the target. According to some embodiments, reducing the relative amount of light from the second light source—the light source that lacks the portion of the visible spectrum—may increase the contrast between different portions of a target tissue illuminated by the light, which may enhance the appearance of a feature of interest. However, reducing the relative amount of light emitted by the second light source, thereby reducing the amount of light in the omitted portion of the visible spectrum, may increase the unnatural appearance of the tissue, which may be undesirable for some users. Accordingly, in some embodiments, a surgical light can enable a user to select the mixture of the light from the first and second light sources. In some embodiments, the surgical light may include preset mixtures of light from the first and second light sources, such as all first spectrum light, all second spectrum light, 50% first spectrum light, 25% first spectrum light, 10% first spectrum light, etc.

According to some embodiments, the relative mix of light from the first and second light sources is adjusted by adjusting the power supplied to one or both of the second light sources. In some embodiments, the relative mix of light from the first and second light sources is adjusted while maintaining the total amount of light at the target. For example, in transitioning from a 50-50 mode in which 50% of the light at the target is provided by each of the first and second light sources to a 100% first light source mode, the power supplied to the first light source may be doubled. In some embodiments, the amount of light provided by the first and/or second light sources to maintain the total amount of light at the target may be adjusted by turning one or more light emitters on and off. For example, for doubling the light from the first or second light source, the number of emitters of the first or second light source that are activated may be doubled.

In some embodiments, the user may select the mix of first and second spectrum light via a user interface on the surgical light, such as a switch on the housing or on the handle used to reposition the light. In some embodiments, the user may select the mix of light using an interface on one or more controllers that are operatively connected to the surgical light. For example, a user may provide an input to a remote control or a microphone connected to a controller that provides a command to the surgical light (e.g., via a wired or wireless connection) to alter the mix of light.

Figure 13:
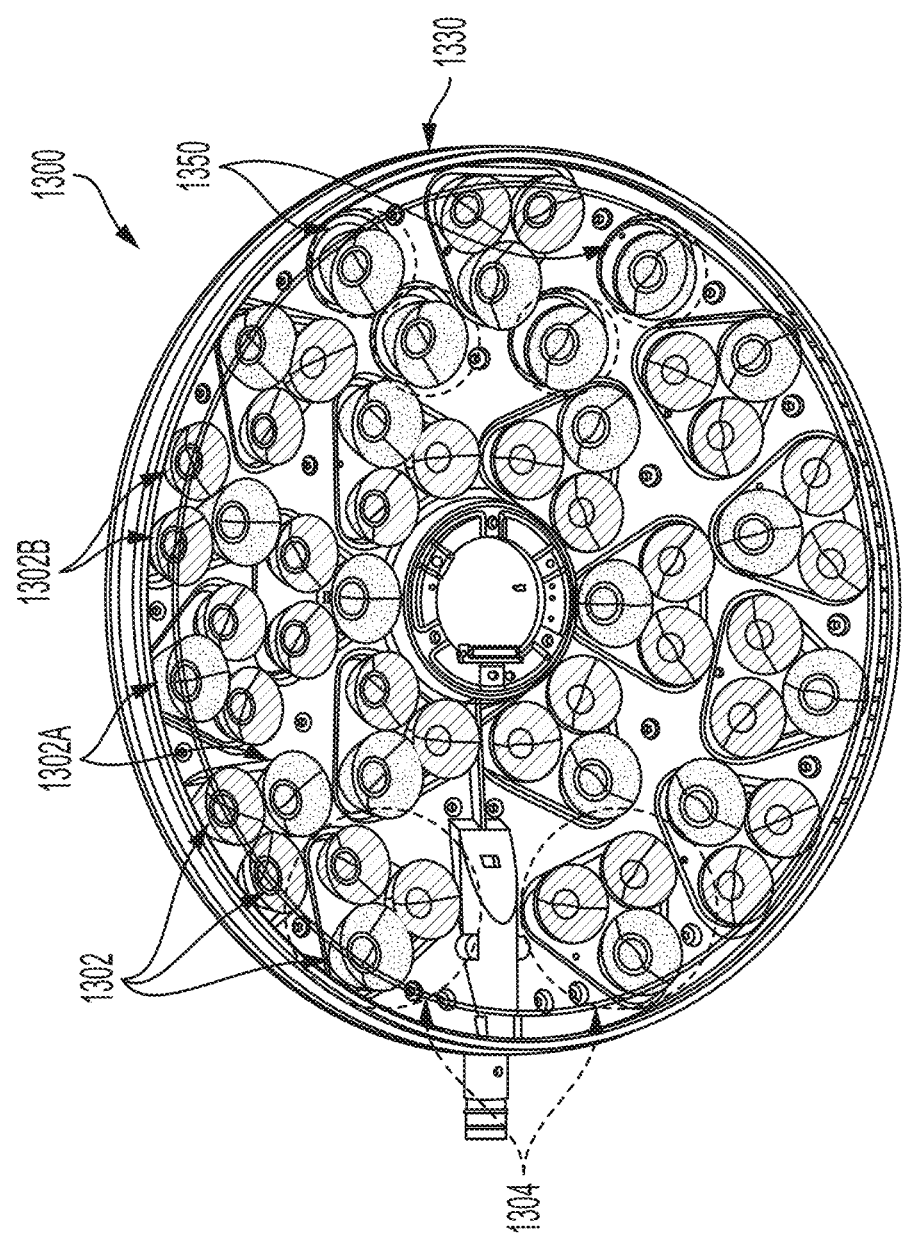
FIG. 13 illustrates a surgical light configured for adjustable illumination spectrum, adjustable brightness, and adjustable spot size, according to some embodiments.

FIG. 13 illustrates a surgical light 1300 that is configured for adjustable illumination spectrum, adjustable brightness, and adjustable spot size, according to various embodiments. According to various embodiments, surgical light 1300 can be used for the surgical light 102 of system 100. As discussed further below, surgical light 1300 includes a plurality of light generating units 1302 that can emit an adjustable spectrum of light for illuminating the tissue of a subject. The surgical light 1300 can include multiple different sets of light generating units 1302 that generate different spot sizes and/or shapes at the target, enabling the adjustment of spot size at the target via adjustment of the relative intensities of the differing sets of light generating units. According to various embodiments, the light generating units 1302 include at least two different light sources that can be controlled to provide adjustable mixtures of the light from the different light sources at the target, in accordance with the principles discussed above with respect to system 100 of FIG. 1.

According to various embodiments, at least some of the light generating units 1302 include multiple light emitters that generate different spectra of light and that can be controlled to provide an adjustable mixture of the spectra to achieve a desired spectrum and intensity of illumination at the target. As discussed further below, light generating units 1302 that include multiple emitters emitting different spectra can include one or more optical components for mixing the different spectra at the light generating unit 1302. Mixing the different light spectra within the surgical light 1300, not at the target, avoids undesirable effects that can occur when different colors are mixed at the target, such as color ringing.

The surgical light 1300 can include any suitable arrangement of light generating units, including light generating units that generate an adjustable spectrum and/or adjustable spot size and one or more light generating units that do not generate an adjustable spectrum and/or adjustable spot size. In the illustrated embodiment, four "micro-spot" light generating units 1350 are configured for generating a small light spot at the target and may not include adjustable color and/or adjustable spot size.

According to some embodiments, the surgical light 1300 includes a curved chassis 1330 that allows the light generating units mounted thereon to be oriented toward a single spot at the presumed position of the illumination target (task plane).

According to various embodiments, the surgical light 1300 includes a first set of light generating units 1302A that are configured and arranged to generate a first illumination pattern at the target and a second set of light generating units 1302B that are configured and arranged to generate a second illumination pattern at the target. According to various embodiments, the relative intensities of the sets of light generating units 1302A,B can be varied to produce different illumination spot patterns at the target.

Figure 14:
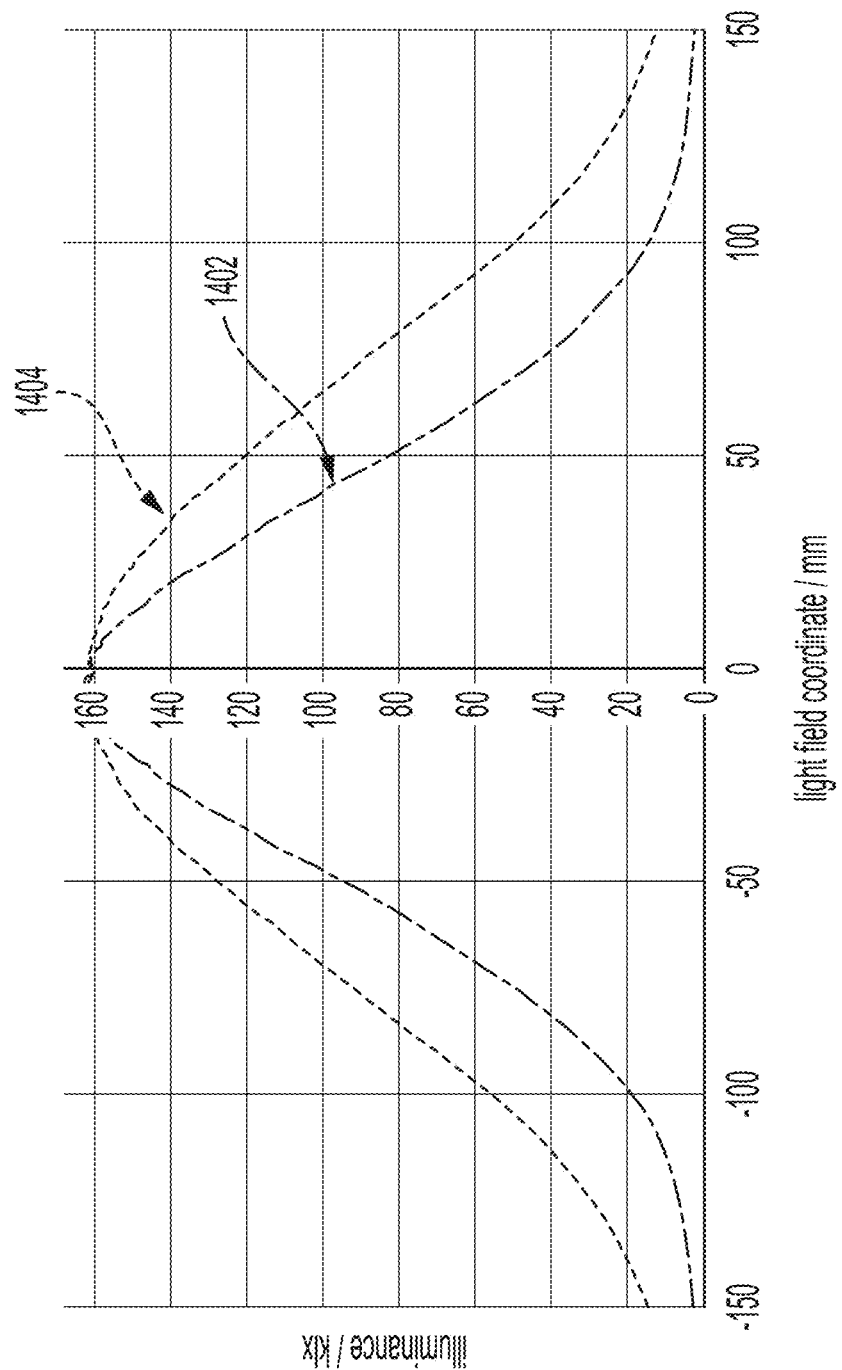
FIG. 14 illustrates examples of the illumination pattern at a target generated by the first and second sets of light generating units, according to some embodiments.

FIG. 14 illustrates examples of the illumination pattern 1402 at a target generated by the first set of light generating units 1302A and the illumination pattern 1404 at the target generated by the second set of light generating units 1302B, according to some embodiments. In the illustrated embodiment, the first set of light generating units 1302A are configured to generate a smaller circular illumination pattern at the target than the second set of light generating units 1302B. The surgical light 1300 can be controlled to vary the relative intensities of the two sets of light generating units to produce different spot sizes.

Figures 15A, 15B, 15C, 15D, 15E:
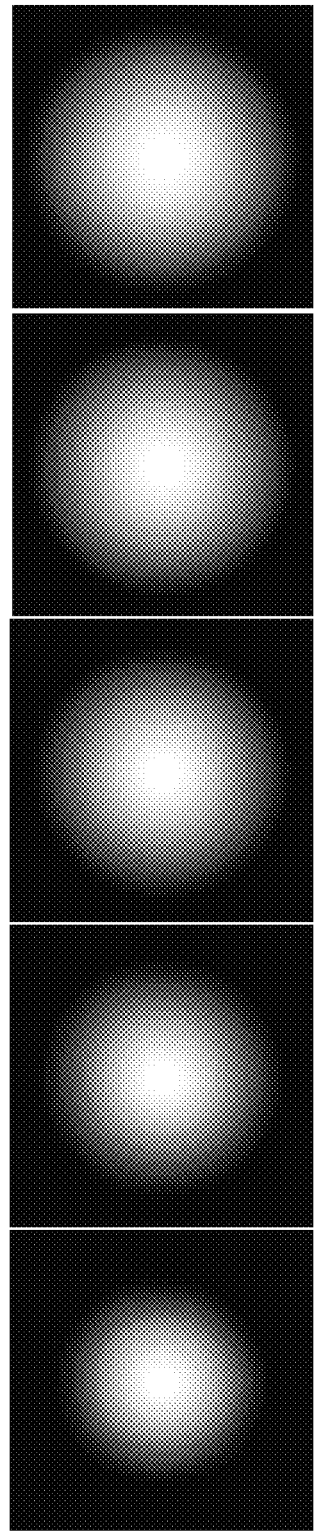
FIGS. 15A-E illustrate different spot sizes produced by varying the relative intensities of the light generating by the two sets of light generating units, according to some embodiments.

FIGS. 15A-E illustrate different spot sizes produced by varying the relative intensities of the light generating by the two sets of light generating units 1302A,B of surgical light 1300, according to various embodiments. FIG. 15A illustrates the illumination pattern at the target resulting from providing light from only the first set of light generating units 1302A producing illumination pattern 1402. FIG. 15E illustrates the illumination pattern at the target resulting from providing light from only the second set of light generating units 1302B producing illumination pattern 1404. FIG. 15B illustrates the illumination pattern at the target resulting from 75% contribution from the first light generating unit 1302A and 25% from the second light generating unit 1302B. FIG. 15D illustrates the illumination pattern at the target resulting from providing 75% contribution from the second light generating unit 1302B and 25% from the first light generating unit 1302A. FIG. 15C illustrates the illumination pattern at the target resulting from providing equal contribution from the first and second light generating units.

Thus, according to various embodiments, the illumination pattern at the target can be adjusted by adjusting the relative intensities of the different light generating units 1302A,B. The change in illumination pattern (spot size) can be achieved without any moving parts. In other words, by adjusting the relative intensities of light generating units that are fixed in place but that generate different illumination patterns, the spot size at the target can be adjusted.

Figure 16:
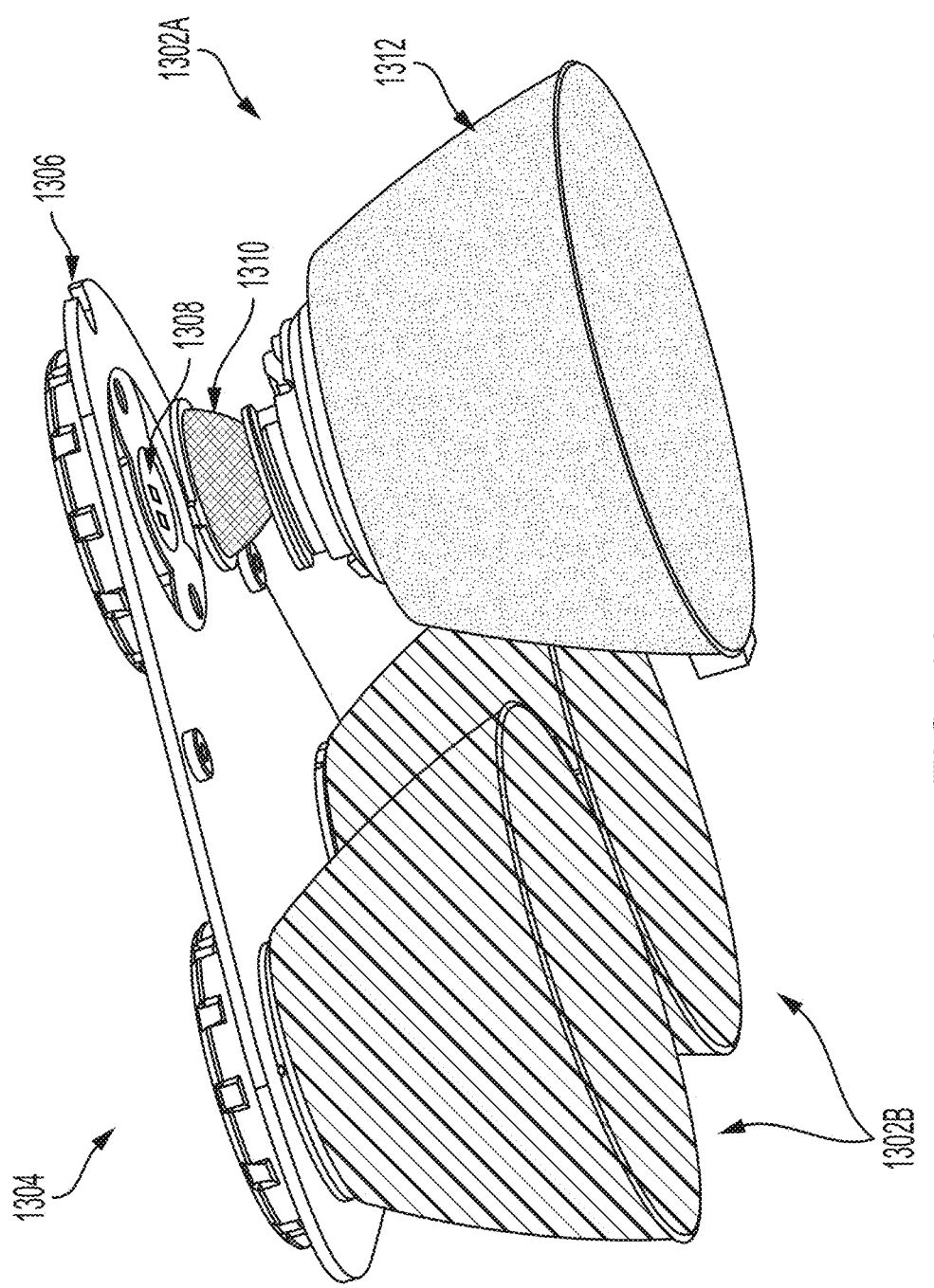
FIG. 16 illustrates a subassembly of light generating units of the surgical light of FIG. 13, according to some embodiments.

According to various embodiments, the light generating units 1302A,B can be arranged in subassemblies 1304 that can be fixedly mounted to the chassis 1330. In some embodiments, each subassembly 1304 includes at least one first light generating unit 1302A and at least one second light generating unit 1302B. An example of a subassembly 1304 is illustrated in FIG. 16. Subassembly 1304 of FIG. 16 includes one first light generating unit 1302A and two second light generating units 1302B. Since the illumination pattern of the second light generating units 1302B can be larger than that of the first light generating units 1302A, the number of second light generating units 1302B in the subassembly 1304 can be greater to provide a similar illuminance at the target. The relative numbers of light generating units 1302A,B is merely exemplary and other embodiments can include any suitable number and combination of first and/or second light generating units 1302A,B.

The light generating units 1304 include a printed circuit board 1306 and a plurality of light emitters 1308 mounted to the printed circuit board, with at least one light emitter 1308 being located at each respective location of the light generating units. Any suitable number of light emitters 1308 can be provided for each light generating unit 1302A,B. At least one optical component is mounted on top of the at least one light emitter 1308 for manipulating the light emitted by the at least one light emitter 1308. In the illustrated embodiment, the first light generating unit 1302A includes a first optical component 1310 that is positioned over the at least one light emitter 1308 and a second optical component 1312 that is positioned over the first optical component. According to various embodiments, the first optical component 1310 is configured to mix (homogenize) the light emitted by light emitters 1308 and, therefore, may be the same for both the first and second light generating units 1302A,B. In some embodiments, the second optical component 1312 is configured to produce the illumination pattern at the target, and, therefore, the second optical component may be different for the second light generating unit 1302B than for the first in order to produce a different illumination patterns at the target.

According to various embodiments, the light generating units 1302A,B are configured for generating light have an adjustable spectrum. The light generating units 1302A,B can each include multiple light emitters 1308 that generate different light spectra. The spectrum of the light emitted by the light generating unit, as well as the illuminance, can be adjusted by varying the relative intensity of the light emitters 1308 of the light generating unit. One or more optical components of the light generating unit can be configured to combine the light from the emitters such that the light from the emitters is mixed at the light generating unit, rather than at the target.

An example of a light generating unit 1302A,B, according to some embodiments, is light generating unit 300 of FIG. 3. The light generating unit 300 configured for the light generating units 1302A,B includes at least one first light emitter 302 that emits light having a first spectrum and at least one second light emitter 302a having a second light spectrum that is different than the first. In some embodiments, the first light spectrum is a white light having a first color temperature and the second light spectrum is a white light having a second color temperature that is different from the first (for example, warm white 2800K and cool white 6500K). The spectrum of the light generated by the light generating unit 1302A,B can be adjusted in the range from the first color temperature to the second color temperature by varying the relative intensities of the emitters. According to some embodiments, one or more emitters generates narrower band light, such as a single color of light. Any suitable number of first and second light emitters 302, 302a can be used. In some embodiments, the light generating unit includes light emitters generating more than two different spectra, such as red, green, and blue emitters.

The light generating unit 300 configured for the light generating units 1302A,B can include a first optic element 306 that is configured for integrating the light from the emitters 308. The first optic element 306 can be, for example, a micro-lens array that includes a plurality of Köhler channels (e.g., each facet of first optic element 306 of FIG. 3 and each facet of first optical component 1310 of FIG. 16) that are configured for imaging the source in each channel, which results in a homogeneous color distribution at the target.

A second optic element 308 is configured to collimate and/or focus the light from the first optic element 306. The second optic element 308 can be a total internal reflection (TIR) element. According to some embodiments, the second optic element 308 is different for the first and second light generating units 1302A,B in order to create different illumination spot sizes at the target. For example, the second optic element 308 for the first light generating unit 1302A can be configured to generate a smaller spot size at the target than the second optic element 308 of the second light generating unit 1302B.

According to various embodiments, the light generating units 1302A,B can be configured to generate reduced spectrum light or to produce light that has a lower contribution from a portion of the spectrum, according to the principles discussed above. For example, one or more of the light generating units 1302A,B can include a filter such as illustrated in FIGS. 4A and 4B that filters out a portion of the spectrum generated by the light emitters. In some embodiments, one or more of the light generating units 1302A,B can be configured to mix a broad spectrum light from a first emitter 302 with a light that omits a portion of the spectrum from a second emitter 302a, resulting in generating light having the broad spectrum but with a reduced contribution from the omitted portion of the spectrum, such as shown in FIG. 5.

Figure 17:
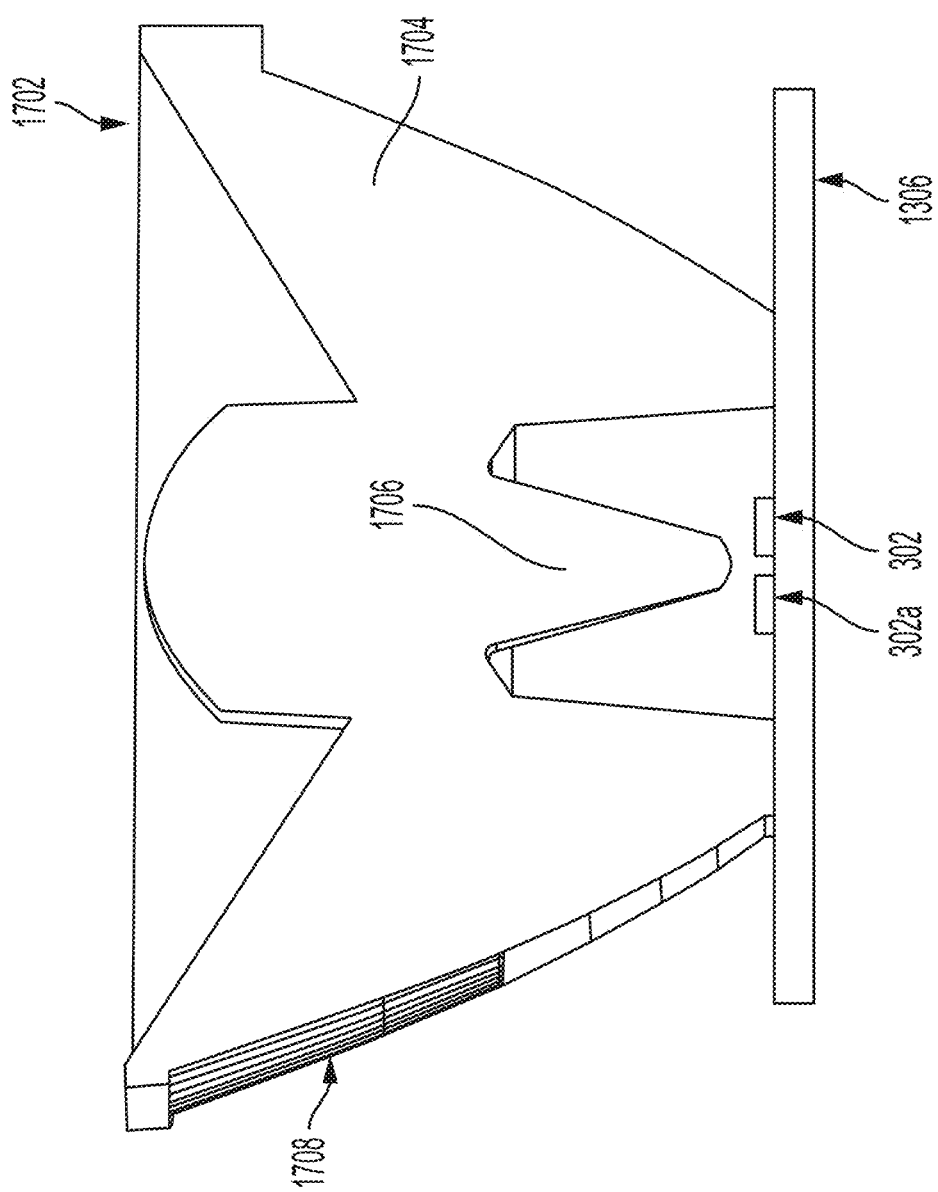
FIG. 17 illustrates an optical arrangement for mixing and directing the light emitted by the light emitters of light generating units, according to some embodiments.

FIG. 17 illustrates an alternative optical arrangement for mixing and directing the light emitted by the light emitters of the first and second light generating units 1302A,B, according to various embodiments. The emitters 302, 302a are covered by a single optic element 1702 that includes a TIR portion 1704 combined with a central Köhler-channel 1706 instead of a lens. A portion 1708 of the outer surface of the TR portion 1704 can be facetted to blur the images of the different emitters 302, 302a in the light field for better mixing.

Figure 18:
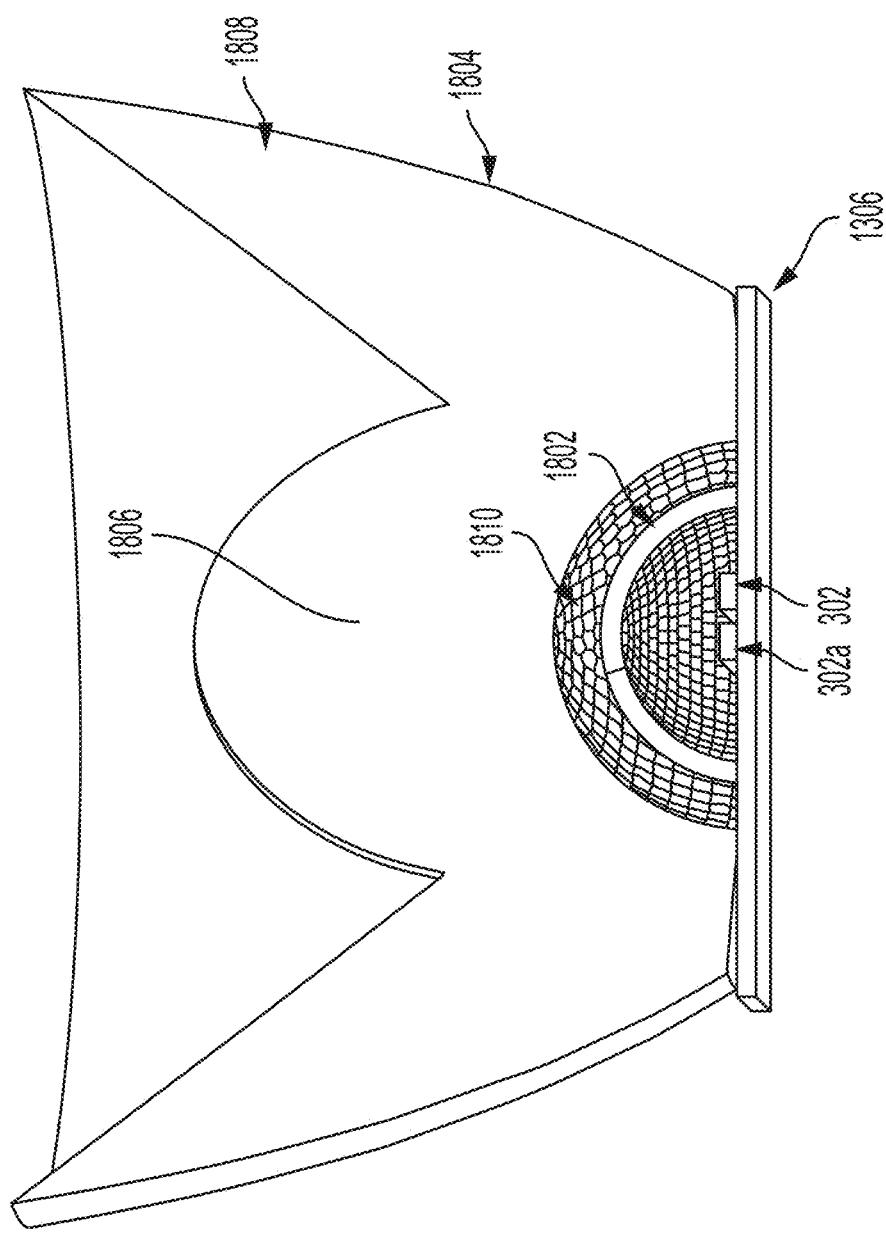
FIG. 18 illustrates an alternative optical arrangement for mixing and directing the light emitted by the light emitters of light generating units, according to various embodiments.

FIG. 18 illustrates another alternative optical arrangement for mixing and directing the light emitted by the light emitters of the first and second light generating units 1302A, B, according to various embodiments. The optical arrangement of FIG. 18 includes a first optic element 1802 that covers the emitters 302, 302a and a second optic element 1804 that covers the first optic element 1802. The first optic element 1802 provides the function of the inner facing lenses of a micro-lens array and images the source (the emitters 302, 302a) in a corresponding lens 1810 of the second optic element 1804. The first lenses of the second optic element 1804 image the main level of the corresponding lenses of the first optic element 1802 virtual back to the source. The central main lens portion 1806 and the TIR portion 1808 image the virtual source in the light field.

Figure 19:
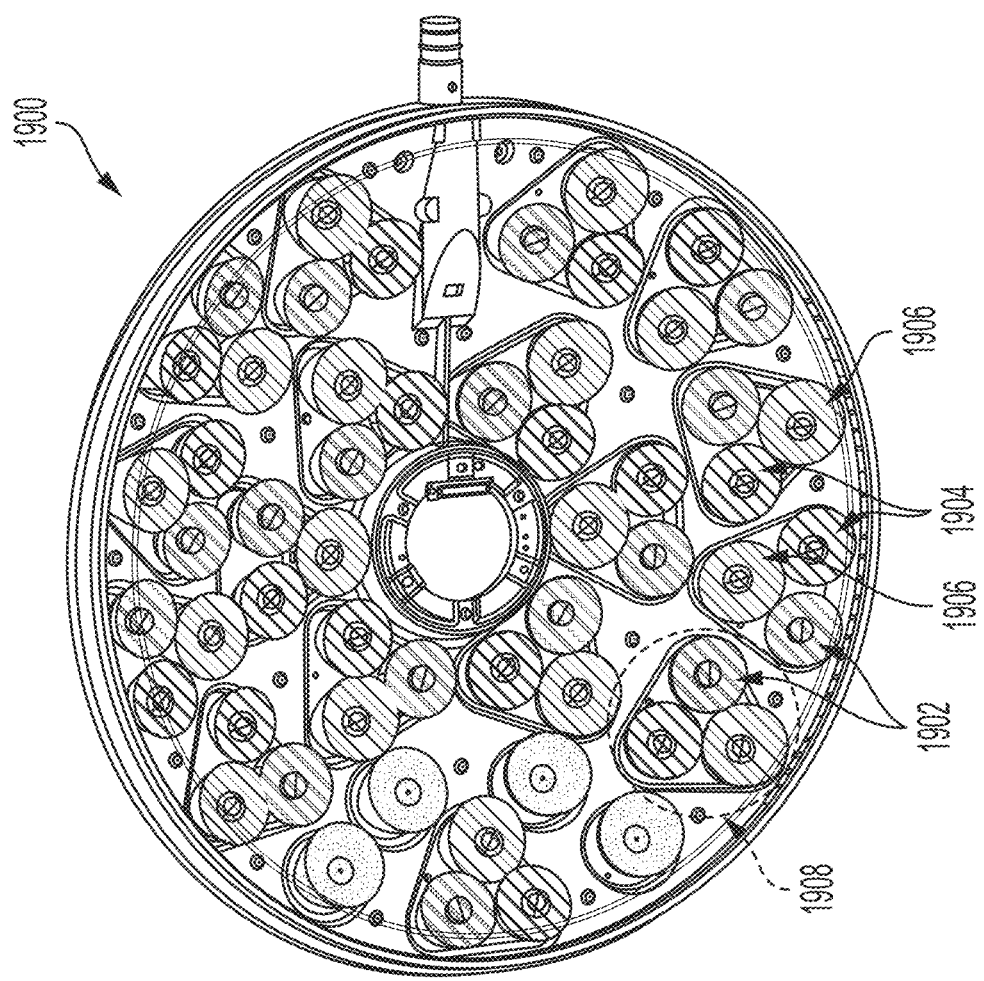
FIG. 19 illustrates a surgical light that includes three different light generating units for generating three different illumination patterns at the target, according to some embodiments.

FIG. 19 illustrates a surgical light 1900 that is similar to surgical light 1300 of FIG. 13, except that each light generating subassembly includes three different light generating units for generating three different illumination patterns at the target, in contrast to the two different light generating units of surgical light 1300. Surgical light 1900 include a plurality of first light generating units 1902 configured for generating a first illumination pattern at the target, a plurality of second light generating units 1904 configured for generating a second illumination pattern at the target, and a plurality of third light generating units 1906 for generating a third illumination pattern at the target. The illumination pattern at the target can be varied by adjusting the relative intensities of the first, second, and third light generating units.

Figure 20:
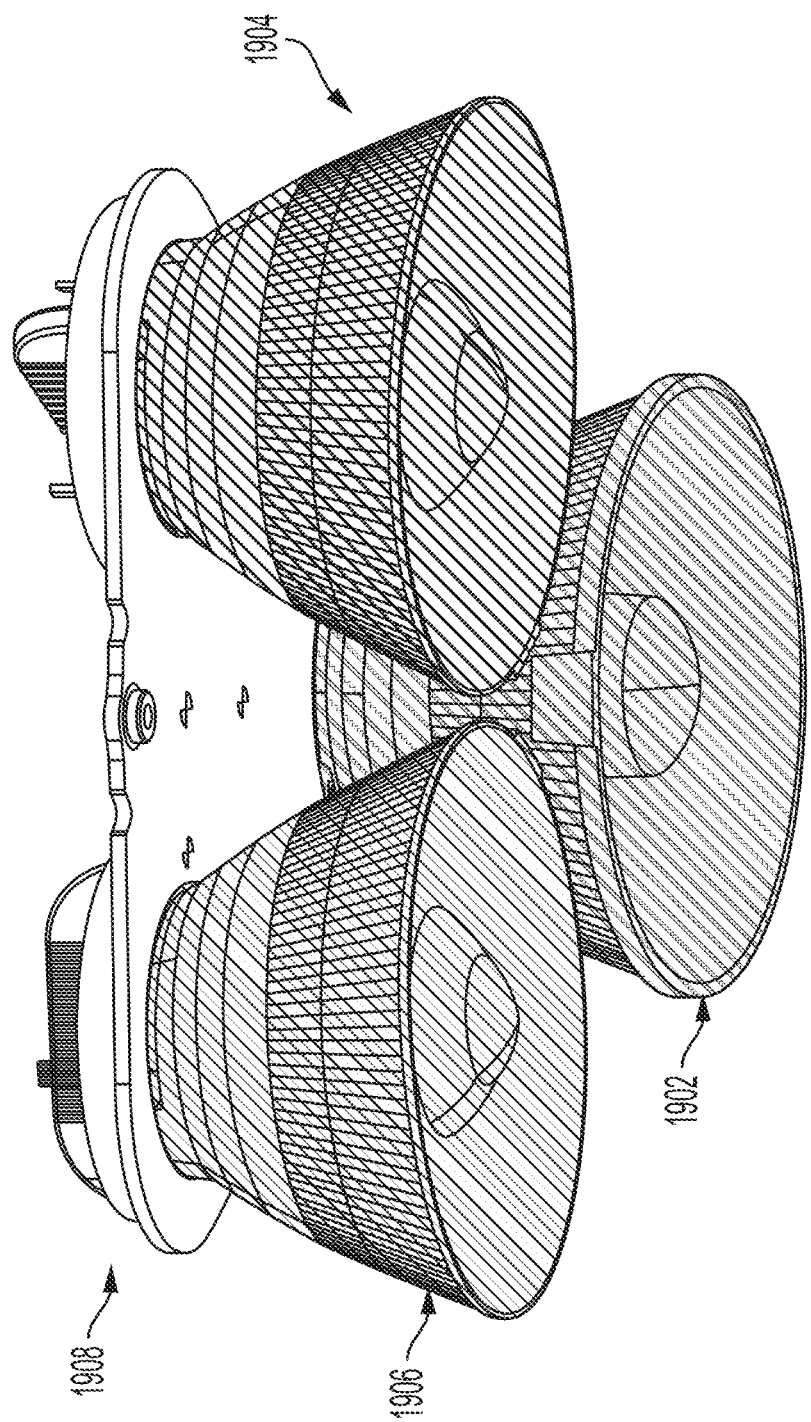
FIG. 20 illustrates a subassembly of light generating units of the surgical light of FIG. 19, according to some embodiments.

According to various embodiments, the three light generating units can be arranged in a plurality of subassemblies 1908. An example of a subassembly 1908 is illustrated in FIG. 20. Subassembly 1908 can include one of each of the first, second, and third light generating units 1902, 1904, 1906.

Figure 21:
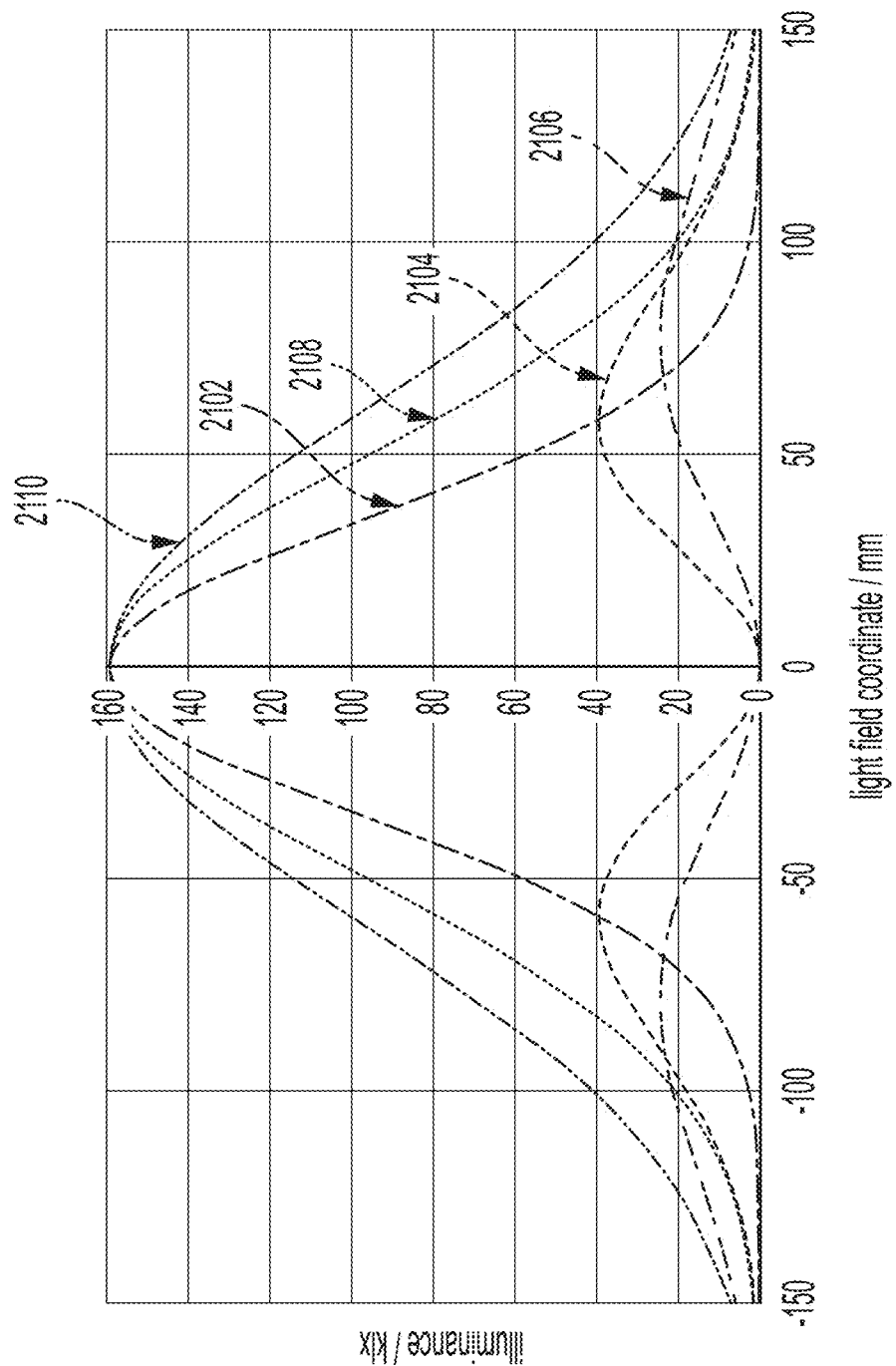
FIGS. 21 and 22A-C illustrate examples the different illumination patterns generated by the three different light generating units, according to various embodiments, with FIG. 21 illustrating the illuminance across the light field and FIGS. 22A-C illustrating the simulated illumination patterns.
Figure 22A:
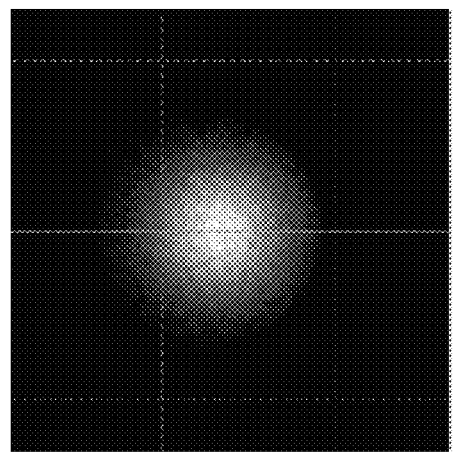
Figure 22B:
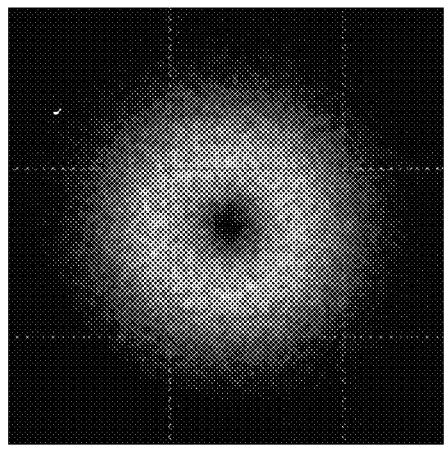
Figure 22C:
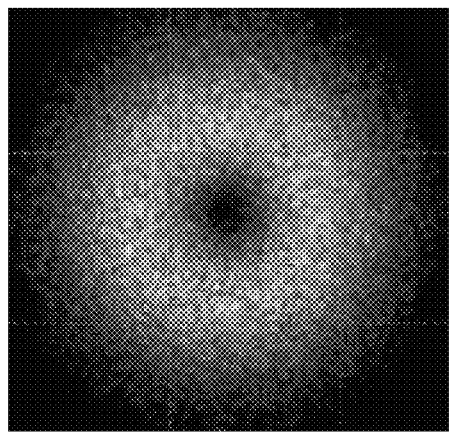

FIGS. 21 and 22A-C illustrate examples the different illumination patterns generated by the three different light generating units, according to various embodiments, with FIG. 21 illustrating the illuminance across the light field and FIGS. 22A-C illustrating the simulated intensities. The first light generating unit 1902 can generate first illumination pattern 2102 (FIG. 22A), second light generating unit 1904 can generate second illumination pattern 2104 (FIG. 22B), and third light generating unit 1906 can generate third illumination pattern 2106 (FIG. 22C). The first illumination pattern 2102 can be a circular pattern with the highest intensity at the center. The second and third illumination patterns 2104, 2106 are annular patterns that have zero intensity in the center. The third illumination patterns 2106 has a wider spread than the second illumination pattern 2104. The relative intensities of the first, second, and third light generating units can be varied to generate different illumination spot sizes. For example, light from the first and second light generating units 1902, 1904 can combine to provide the illumination pattern represented by dashed line 2108. Addition of light from the third light generating unit 1906 can provide the illumination pattern represented by dashed line 2110.

According to various embodiments, the light generating units (such as light generating units 1302A,B and light generating units 1902-1906) can be controlled by a controller (such as controller 122 of FIG. 1) to generate the desirable light spectrum, intensity, and/or spot size at the target. According to various embodiments, the subassemblies of light generating units (such as subassembly 1304 or subassembly 1908) are operated identically to one another. For example, for a given spot size, the relative intensities of the light generating units will be substantially the same from one subassembly to the next. Similarly, according to various embodiments, the spectrum from at least a portion of the light generating units can be identical from one light generating unit to the next. In some embodiments, the spectrum generated by each light generating unit is the same.

Accordingly, according to some embodiments, a method for adjusting a spot size from a surgical light, such as surgical light 1300 of FIG. 13 or surgical light 1900 of FIG. 19, includes receiving a command for a spot size at a controller of the surgical light and, in response, the controller adjusting the intensities of the set of first light generating units (each generating a first illumination pattern) and/or the intensities of the set of second light generating units (each generating a second illumination pattern) and/or other light generating units (generating other illumination patterns) until the commanded spot size is achieved. The commanded spot size can be achieved via just one set of light generating units, with fewer than all sets of light generating units, or with a combination of all light generating units. In some embodiments, all of the first light generating units of the surgical light are commanded to the same intensity level. Similarly, all of the second light generating units of the surgical light can be commanded to the same intensity level, which can be the same as or different than the intensity level of the first light generating units. According to various embodiments, the relative intensity levels of the first and second light generating units (and other light generating units if applicable) can be adjusted based on maintaining a predetermined illuminance at the target. For example, where a larger spot size is commanded by the user, the intensity of the light provided by the larger spot size light generating units can be increased in response to the user's command, and to maintain the illuminance level at the target, the intensity of the light provided by the smaller spot size light generating units can be decreased.

According to various embodiments, a method for adjusting the spectrum of light at the target from a surgical light, such as surgical light 1300 of FIG. 13 or surgical light 1900 of FIG. 19, includes receiving a command for a desired spectrum (e.g., a desired white light color temperature) at a controller of the surgical light and, in response, the controller adjusting the relative intensities of at least two different emitters emitting at least two different spectra of the light generating units to achieve the desired spectrum at the target. According to various embodiments, each light generating unit having the at least two different emitters is driven identically to the other light generating units so that all light generating units having the at least two different emitters emit light having the same spectrum.

According to various embodiments, a command for adjusting the spot size and/or spectrum of light provided by the surgical light according to any of the systems and method described herein can be received via any suitable user input, including but not limited to one or more selectors on a housing of the surgical light, via a knob of the surgical light, via a wall control communicatively coupled to the surgical light, via some other remote control for the surgical light, or via an imaging system communicatively coupled to the surgical light, or via any other suitable user input. In some embodiments, spot size, spectrum, and/or any other aspect of the light provided by the surgical light can be modified based on a command from a system, such as an imaging system, that monitors one or more parameters of the surgical scene and adjusts the lighting provided by the surgical light to maintain and/or achieve a predetermined characteristic of illumination of the target. For example, the imaging system may monitor a level of red reflecting from the surgical scene and may command the surgical light to reduce the relative contribution of red in the illumination.

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

The invention claimed is:

1. A surgical light for illuminating a target with light that has a reduced contribution of a red portion of the visible spectrum, comprising:
    a first light source comprising at least one white light emitter that is configured to emit white light;
    a second light source comprising at least one white light emitter that is the same type of white light emitter as the white light emitter of the first light source and at least one filter configured to filter only a red portion of the white light emitted by the at least one white light emitter of the second light source; and
    a controller configured to simultaneously activate the first and second light sources for illuminating the target with light that has a reduced contribution of light in the red portion of the visible spectrum relative to white light.

2. The surgical light of claim 1, wherein the controller is configured to control the relative amount of light provided by the first and second light sources to adjust the relative contribution of light in the red portion of the visible spectrum to the light at the target.

3. The surgical light of claim 1, wherein the controller is configured to adjust the contribution of light in the red portion of the visible spectrum while maintaining a constant illuminance at the target.

4. The surgical light of claim 1, wherein the second light source comprises at least one optic and the at least one filter is disposed on the at least one optic.

5. The surgical light of claim 4, wherein the at least one optic comprises a lens.

6. The surgical light of claim 4, wherein the at least one optic comprises a mirror.

7. The surgical light of claim 1, wherein the second light source comprises at least one optic and the filter is disposed between the at least one white light emitter and the at least one optic.

8. The surgical light of claim 1, wherein the at least one white light emitter of each of the first and second light sources each comprise at least one solid state white light emitter.

9. The surgical light of claim 1, wherein at least one of the first light source and the second light source comprises a plurality of white light emitters having different color temperatures.

10. The surgical light of claim 1, wherein at least one of the first and second light sources comprises a plurality of light generating units, each light generating unit comprising the at least one white light emitter and at least one optic for manipulating light emitted by the at least one white light emitter.

11. The surgical light of claim 10, wherein each light generating unit comprises a plurality of white light emitters.

12. The surgical light of claim 11, wherein each light generating unit comprises an optical integrator for integrating light from the plurality of white light emitters.

13. The surgical light of claim 10, wherein at least one light generating unit of the second light source comprises the filter disposed on the at least one optic.

14. The surgical light of claim 13, wherein the filter is disposed on an outer surface of the at least one optic that faces away from the at least one white light emitter.

15. The surgical light of claim 13, wherein the filter is disposed on an inner surface of the at least one optic that faces toward the at least one white light emitter.

16. The surgical light of claim 10, wherein light generating units of the first light source are interspersed with light generating units of the second light source.

17. The surgical light of claim 1, wherein the controller is configured to simultaneously activate the first and second light sources in a first mode and to deactivate the second light source in a second mode for illuminating the target with only the white light emitted by the at least one white light emitter of the first light source.

18. A method for illuminating a target with light that has a reduced contribution of a red portion of the visible spectrum, the method comprising:
    emitting white light from at least one white light emitter of a first light source;
    simultaneously emitting white light from at least one white light emitter of a second light source, wherein the at least one white light emitter of the second light source is the same type of white light emitter as the white light emitter of the first light source;
    filtering only a red portion of the white light emitted by the at least one white light emitter of the second light source by a filter of the second light source; and
    illuminating the target with light from the first and second light sources simultaneously such that the target is illuminated by light that has a reduced contribution of light in the red portion of the visible spectrum relative to white light.

19. A surgical light for illuminating a target with light that has a reduced contribution of a single spectral range of the visible spectrum, comprising:
    a first light source configured to emit light having a first spectrum that includes the single spectral range of the visible spectrum;
    a second light source configured to emit light having a second spectrum that includes the first spectrum except for the single spectral range of the visible spectrum; and
    a controller configured to simultaneously activate the first and second light sources for illuminating the target with light that has a reduced contribution of light in the single spectral range of the visible spectrum relative to white light,
    wherein the controller is configured to switch from a first mode in which the first and second light sources are simultaneously activated to a second mode in which the second light source is deactivated, and to control the first and second light sources to provide the same illuminance at the target in both the first and second modes.

20. The surgical light of claim 19, wherein the first light source comprises at least one white light emitter configured to emit white light.

21. The surgical light of claim 20, wherein the second light source comprises at least one white light emitter that is the same type of white light emitter as the white light emitter of the first light source and at least one filter configured to filter only the single spectral range of the white light emitted by the at least one white light emitter of the second light source.

22. The surgical light of claim 21, wherein the single spectral range is a red portion of the visible spectrum.

23. The surgical light of claim 19, wherein the second spectrum has a narrower spectral range than the first spectrum.

24. The surgical light of claim 23, wherein the first spectrum includes the second spectrum.

25. The surgical light of claim 19, wherein the single spectral range of the visible spectrum comprises at least a portion of the red portion of the visible spectrum.

26. The surgical light of claim 19, wherein the second light source comprises at least one emitter that is configured to emit light across the second spectrum but not in the single spectral range of the visible spectrum.

27. The surgical light of claim 19, wherein the second light source comprises at least one light emitter configured to emit light across at least a portion of the first spectrum and at least one filter for filtering out light in the single spectral range of the visible spectrum.

28. The surgical light of claim 19, wherein the first light source comprises a plurality of narrow band light emitters having different spectral ranges that collectively emit the light having the first spectrum.

\* \* \* \* \*